United States Patent [19]
Leder et al.

[11] Patent Number: 5,473,939
[45] Date of Patent: Dec. 12, 1995

[54] METHOD AND APPARATUS FOR PRESSURE, VOLUME, AND TEMPERATURE MEASUREMENT AND CHARACTERIZATION OF SUBSURFACE FORMATIONS

[75] Inventors: John L. Leder, Bellaire; John M. Michaels, Houston; Than Shwe, Houston; John C. Anderson, Houston, all of Tex.

[73] Assignee: Western Atlas International, Inc., Houston, Tex.

[21] Appl. No.: 48,814

[22] Filed: Apr. 16, 1993

Related U.S. Application Data

[63] Continuation-in-part of Ser. No. 903,088, Jun. 19, 1992, abandoned.

[51] Int. Cl.⁶ .................................................. E21B 47/00
[52] U.S. Cl. ............................ 73/155; 73/151; 166/264
[58] Field of Search ........................... 73/155, 861.01, 73/861.02, 19.1, 64.45, 61.47, 151; 166/264, 305.1, 100; 417/63, 534–546; 436/25, 30

[56] References Cited

U.S. PATENT DOCUMENTS

| | | | |
|---|---|---|---|
| 3,611,799 | 10/1971 | Davis | 73/155 |
| 3,657,925 | 4/1972 | Gross | 73/239 |
| 3,813,936 | 6/1974 | Urbanosky et al. | 73/155 |
| 4,339,948 | 7/1982 | Hallmark | 73/155 |
| 4,535,843 | 8/1985 | Jageler | 73/151 |
| 5,051,074 | 9/1991 | Cowan | 417/535 |
| 5,106,272 | 4/1992 | Oakley et al. | 417/63 |
| 5,195,588 | 3/1993 | Dave | 166/264 |
| 5,303,775 | 4/1994 | Michaels et al. | 166/264 |
| 5,337,822 | 8/1994 | Massie et al. | 73/155 |

*Primary Examiner*—Robert J. Warden
*Assistant Examiner*—Hien Tran
*Attorney, Agent, or Firm*—James L. Jackson; Darryl M. Springs

[57] ABSTRACT

A method and apparatus for conducting in situ tests on a subsurface earth formation of interest which is traversed by a wellbore. A wireline formation testing instrument is positioned at formation depth and a sampling probe thereof is extended into fluid communication with the formation and isolated from wellbore pressure. Utilizing a hydraulically energized double-acting bi-directional piston pump and by valve controlled selection of pumping direction testing fluid such as completion fluid may be pumped into the formation through the sampling probe either from fluid reservoirs of the instrument or from the wellbore. After reversing the operating and control valving of the pump and instrument, the piston pump is utilized to extract formation fluid from the formation and pump it to sample tanks of the instrument, pump it into the wellbore or subject it to controlled pressure for real time formation testing and for formation characterization. The pumping mechanism of the formation testing instrument includes a pump-through capability for unlimited pumping of formation fluid to permit effective removal of filtrate, sand, rocks and other debris until an uncontaminated formation fluid sample can be recovered for testing. The piston pump and valving arrangement further permits successive draw-down of minute volumes for rapidly determining formation pressure and permits bubble point pressure and fluid compressibility testing to enable bubble point pressure and fluid compressibility profile plots for formation characterization.

29 Claims, 8 Drawing Sheets

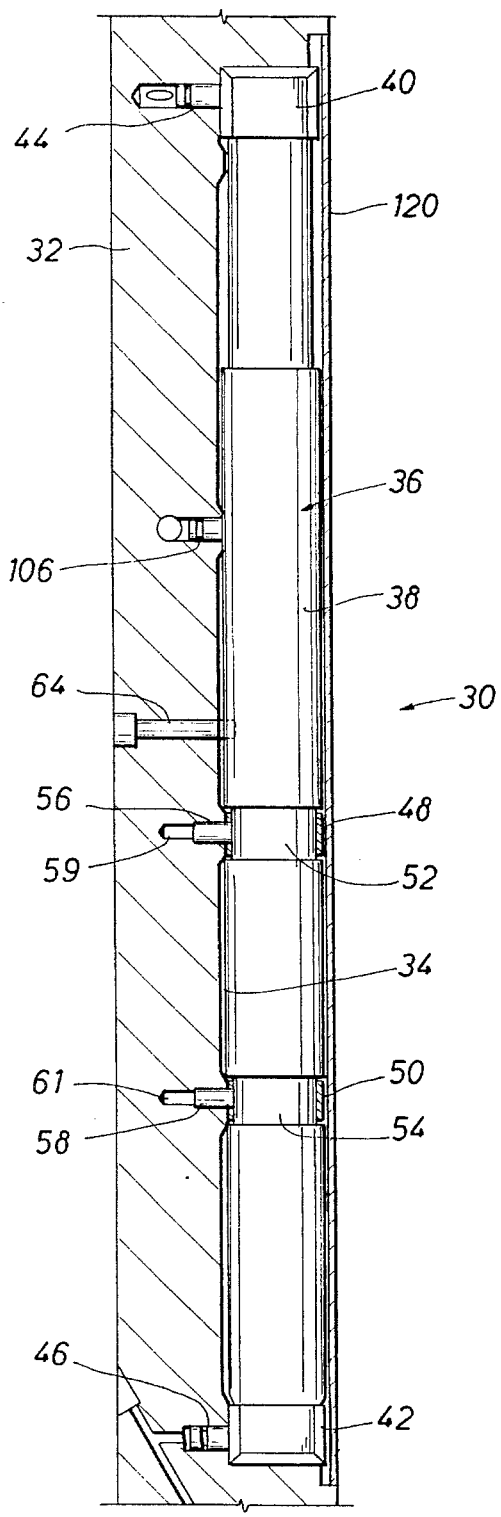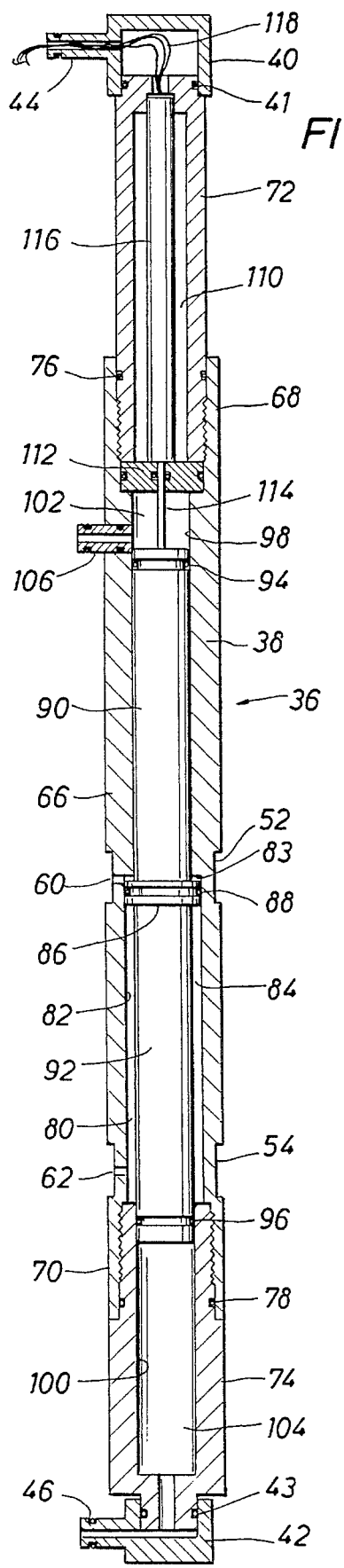

METHOD AND APPARATUS FOR PRESSURE, VOLUME, AND TEMPERATURE MEASUREMENT AND CHARACTERIZATION OF SUBSURFACE FORMATIONS

This is a continuation-in-part of application Ser. No. 07/903,088 filed on Jun. 19, 1992, by John T. Leder, Than Shwe and John M. Michaels entitled Method and Apparatus For Pressure, Volume, and Temperature Measurement of Subsurface Formations, now abandoned.

FIELD OF THE INVENTION

This invention relates generally to a method and apparatus for subsurface formation testing, and more particularly concerns methods and apparatus for providing real time simultaneous measurements of the response:; to changes in pressure, volume and/or temperature of fluid samples from subsurface earth formations traversed by a wellbore for conducting in situ tests for determination of factors influencing potential formation productivity and for acquiring connate fluid samples in sample tanks under conditions of controlled pressure for subsequent laboratory analyses. Such in situ tests include determination of fluid bubble point pressure at formation depth and under formation conditions and determination of fluid compressibility and use of the same for reservoir characterization by means of bubble point pressure and fluid compressibility profile plots.

BACKGROUND OF THE INVENTION

The sampling of fluids contained in subsurface earth formations provides a method of testing formation zones of possible interest by recovering a sample of any formation fluids present for later analysis in a laboratory environment while causing a minimum of damage to the tested formations. The formation sample is essentially a point test of the possible productivity of subsurface earth formations. Additionally, a continuous record of the sequence of events during the test is made at the surface. From this record, valuable formation pressure and permeability data as well as data determinative of fluid compressibility and relative viscosity can be obtained for formation reservoir analysis.

Early formation fluid sampling instruments such as the one described in U.S. Pat. No. 2,674,313 were not fully successful as a commercial service because they were limited to a single test on each trip into the borehole. Later instruments were suitable for multiple testing; however, the success of these testers depended to some extent on the characteristics of the particular formations to be tested. For example, where earth formations were unconsolidated, a different sampling apparatus was required than in the case of consolidated formations.

Down-hole multi-tester instruments have been developed with extensible sampling probes for engaging the borehole wall at the formation of interest for withdrawing fluid samples therefrom and measuring pressure. In downhole instruments of this nature it is typical to provide an internal draw-down piston which is reciprocated hydraulically or electrically to increase the internal volume of a fluid receiving chamber within the instrument after engaging the borehole wall. This action reduces the pressure at the instrument formation interface causing fluid to flow from the formation into the fluid receiving chamber of the tool. Heretofore, the pistons accomplish suction activity only while moving in one direction. On the return stroke the piston simply discharges the formation fluid sample through the same opening through which it was drawn and thus provides no pumping activity. Additionally, unidirectional piston pumping systems of this nature are capable of moving the fluid being pumped in only one direction and thus causes the sampling system to be relatively slow in operation.

Early down-hole multi-tester instruments were not provided with a capacity for substantially continuous pumping of formation fluid. Even large capacity tools have heretofore been limited to a maximum draw-down collection capability of only about 1000 cc and they have not heretofore had the capability of selectively pumping various fluids to and from the formation, to and from the borehole, from the borehole to the formation, or from the formation to the borehole. U.S. Pat. No. 4,513,612 describes a Multiple Flow Rate Formation Testing Device and Method which allows the relatively small volume draw-down to be discharged into the wellbore or to be forced back into the formation. The use of "passive" valves as taught in this method precludes reverse flow. This method does provide for limited or one shot reverse flow much like a hypodermic needle but transferring large volumes of fluid between two reservoirs in a near continuous manner is not achievable with this method. It is desirable, therefore, to provide a down-hole fluid sampling tool with enhanced pumping capability with an unlimited capacity for discharge of formation fluid into the wellbore and with the capability to achieve bi-directional fluid pumping to enable a reverse flow activity that permits fluid to be transferred to or from a formation. It is also desirable to provide a down-hole testing instrument having the capability of selectively pumping differing fluids such as formation fluid, known oils, known water, known mixtures of oil and water, known gas-liquid mixtures, and/or completion fluid to thereby permit in situ determination of formation permeability, relative permeability and relative viscosity and to verify the effect of a selected formation treatment fluid on the producibility of connate fluid present in the formation.

In all cases known heretofore, down-hole multi-test sampling apparatus incorporates a fluid circuit for the sampling system which requires the connate fluid extracted from the formation, together with any foreign matter such as fine sand, rocks, mud-cake, etc. encountered by the sampling probe, to be drawn into a relatively small volume chamber and which is discharged into the borehole when the tool is closed as in U.S. Pat. No. 4,416,152. Before closing, a sample can be allowed to flow into a sample tank through as separate but parallel circuit. Other methods provide for the sample to be collected through the same fluid circuit.

U.S. Pat. No. 3,813,936 describes a "valve member 55" in column 11, lines 10–25 which forces trapped wellbore fluids in a "reverse flow" through a screen member as the "valve member 55" is retracted. This limited volume reverse flow is intended to clean the screen member and is not comparable to bi-directional flow described in this disclosure because of the limited volume.

Mud flitrate is forced into the formation during the drilling process. This flitrate must be flushed out of the formation before a true, uncontaminated sample of the connate fluid can be collected. Prior art sampling devices have a first sample tank to collect flitrate and a second to collect connate fluid. The problem with this procedure is that the volume of flitrate to be removed is not known. For this reason it is desirable to pump formation fluid that is contaminated with flitrate from the formation until uncontaminated connate fluid can be identified and produced. Conventional down-hole testing instruments do not have an unlimited fluid pumping capability and therefore cannot ensure complete flushing of the filtrate contaminant prior to sampling.

Estimates of formation permeability are routinely made from the pressure change produced with one or more drawdown piston. These analyses require that the viscosity of the fluid flowing during pumping be known. This is best achieved by injecting a fluid of known viscosity from the tool into the formation and comparing its viscosity with recovered treated formation fluid.

A reversible pump direction will also allow the fluid to be injected from the tool or borehole into the formation. For example, treatment fluid stored within an internal tank or compartment of the instrument or drawn from the wellbore may be injected into the formation. After injection, additional draw- downs and/or sampling may take place to determine the effect of the treatment or completion fluid on the producibility of the formation. Early formation sampling instruments have not been provided with features to determine the optimum sampling pressures. The present invention also provides a positive method for overcoming differential sticking of the packer.

Determining whether or not thin bed formations are truly connected is a significant concern when completing an oil/gas well for production. This is presently done with pressure gradient plots; however, when the formations are near the same depth, the use of pressure gradient plots may not be conclusive.

An alternative to increasing the accuracy of depth measurement is to examine some other physical characteristic which can also be correlated to common or separate formations. The development of downhole pressure, volume and temperature measurement through employment of apparatus and methods as set forth herein can effectively provide these characteristics.

Bubble point pressure is a physical property of formation fluid which is defined as the pressure at which a gas begins to be liberated from a liquid/gas mixture and a gas bubble begins to form in the fluid at a constant temperature. Bubble point pressure is determined by confining fluid in a known volume and by observing pressure changes as the volume of the fluid is changed. A plot of volume in comparison with pressure will indicate the fluid phase change from one phase (liquid) into two phases (liquid and gas). The intersection of two best fit "volume" and "pressure" lines of the plot indicates the bubble point pressure for the sample fluid.

Once a petroleum field is discovered, it is essential to know details about the fluid content and the geological constraints of the reservoir in order to maximize recovery of the petroleum products therefrom. Most known oil and gas reservoirs are stratified and multilayered. Some producible petroleum reservoirs may be 1000 feet thick and others as thin as 1 foot. The different layers of the reservoir may contain the same type of fluid or may contain fluids of different origins, driven by the same pressure source or driven by different pressure sources. Determining which of these conditions is true before completing a well for production is very significant in efficient recovery of hydrocarbons from the formation or formations that are intersected by the well bore.

Bubble point pressure data has been used for fluid composition analysis using the recombined fluid samples. Such data has not been used heretofore for purposes of reservoir characterization, principally because of the inability to obtain representative fluid samples in quantity, quality and in a timely manner as required for reservoir interpretation. It is therefore desirable to provide a downhole PVT multitester instrument and method for conducting bubble point fluid analysis and determination of fluid compressibility at formation depth and to employ the results thereof for the purpose of reservoir characterization.

The present invention overcomes the deficiencies of the prior art by providing method and apparatus for achieving in situ pressure, volume and temperature (PVT) measurement and bubble point pressure and fluid compressibility analysis. These features are accomplished through utilization of a PVT multitester instrument having a double-acting, bi-directional fluid control system incorporating a double-acting bi-directional piston pump capable of achieving pumping activity in each direction of its linear stroke and capable, through its reciprocating pump stroke and valving activity, of achieving bi-directional fluid flow. The downhole PVT instrument is also capable of selectively discharging acquired connate fluid into the wellbore or into sample containing vessels or pumping fluid from the wellbore or a sample containing vessel into the formation.

For bubble point and fluid compressibility analysis at least one of the pumping chambers of the PVT multitester instrument is designated as a bubble point and fluid compressibility test chamber for valve controlled confinement of a known volume of the formation fluid. By then accurately sensing the temperature and pressure of the trapped volume of fluid, such as by means of precision temperature and pressure sensors in communication with the test chamber, and by selectively changing the volume of the test chamber by piston movement and accurately detecting the volumetric test chamber change, such as by means of a precision controlled linear potentiometer, electronic signals representing fluid temperature pressure and volumetric change can be readily acquired and utilized for bubble point pressure profile plots for use in reservoir characterization.

SUMMARY OF THE INVENTION

It is a principle feature of the present invention to provide a novel method for accomplishing down-hole pressure, volume and temperature measurement of connate fluid being extracted from a formation of interest and for pressurizing or depressurizing the connate fluid sample for the construction of PVT relationship curves which can be used to determine the type of reservoir fluid prior to taking a sample.

It is also a feature of this invention to provide a novel method for pressure volume and temperature measurement of connate fluid present in a subsurface formation of interest wherein the bubble point pressure of fluid is determined in order to set up the optimum sampling pressure for collecting a sample representative of the reservoir condition.

It is another feature of this invention to provide a novel method and apparatus for accomplishing down-hole testing of a subsurface formation to enable the identification of the fluid prior to collection of samples, to determine down-hole bubble point pressure for optimum sampling conditions, to determine fluid properties for pressure transient analysis, and to accomplish acquisition of down-hole pressure volume and temperature data to check the validity of samples at the surface, either on location or at reservoir fluid laboratories.

It is also a feature of the present invention to provide a downhole PVT multitester instrument that has defined therein a test chamber and signal acquisition system for bubble point pressure and fluid compressibility analysis at formation depth to provide for efficient bubble point and fluid compressibility profile plots for use in reservoir characterization.

It is another important feature of this invention to provide controlled draw-down pressure or sample flowing pressure to improve pressure transient analysis of a draw-down and build-up test.

It is another important feature of this invention to provide for control of the injection pressure of fluid being injected into the formation to improve pressure transient analysis of an injection test.

It is another important feature of this invention to accomplish in situ pressure transient analysis in the down-hole environment.

It is another important feature of this invention to determine fracturing pressure of the formation, which is critical data for formation stimulation.

It is another important feature of this invention to provide novel down-hole testing apparatus incorporating a double-acting bi-directional pump which is contained within a draw-down module having a pump through capability and wherein the pump speed can be controlled thus allowing a controlled rate for pressure drop, total volume or rate so as to adapt the test being conducted to the formation characteristics.

It is another feature of this invention to provide novel apparatus for down-hole formation testing which incorporates a pump and valving mechanism enabling the selective pumping of the fluid from the formation to the borehole so as to accomplish removal of all filtrate from the formation before sampling or taking other formation data such as pressure, volume and temperature (PVT), resistivity, compressibility, bubble point, relative viscosity, etc.

It is an even further feature of this invention to provide a novel down-hole testing apparatus incorporating a double-acting bi-directional pump mechanism capable of reversing its pumping direction to allow fluid, such as completion fluid, to be injected from the instrument or borehole into the formation and to accomplish draw-down from the formation for sampling to determine the effect of the fluid being injected into the formation.

It is another important feature of this invention to provide a novel formation testing instrument having a down-hole draw-down pump-through capability and having a double-acting bi-directional pump and valving arrangement capable of accomplishing selective pumping of an unlimited volume of formation fluid from the formation to the wellbore or to collection tanks to clean or flush away any debris such as sand, rocks, filtrate, etc. in the formation surrounding the wellbore or at the interface of the sampling probe with the wellbore wall to ensure the taking of a clean, uncontaminated sample for testing.

It is an even further feature of this invention to provide a novel formation testing instrument having a down-hole draw-down double-acting bi-directional pump mechanism which allows fluid to be injected from the tool or borehole into the formation to determine the effect of the completion fluid on the formation and its constituents.

Briefly, the various features of the present invention are effectively realized through the provision of a down-hole formation testing instrument that is capable of pressurizing an initial small, i.e., in the order of 70 cc volume, for example, of sample fluid to a high pressure range, in the order of about 20,000 psi for example. The sampling instrument is also capable of controllably depressurizing a fluid sample as well. This pressurization and depressurization capability allows for the construction of PVT relationship curves which can be used to determine the type and other desirable characteristics of reservoir fluid prior to taking a sample. PVT tests can be repeated an unlimited amount of times until a clean formation fluid sample is obtained.

The bubble point pressure and compressibility of the formation fluid is determined in order to set up the optimum sampling pressure for collecting a sample representative of the reservoir condition. At least one of the bi-directional piston pump chambers of the instrument is provided with a shutoff valve for fluid entrapment therein and is designated a bubble point pressure and fluid compressibility test chamber having a precision temperature sensor and precision fluid pressure gauge in communication therewith. The piston of the test chamber is coupled with a precision potentiometer for detection of volumetric change of the test chamber. By then selectively changing the volume of the test chamber and the connate fluid entrapped therein and by observing the pressure of the fluid as its volume is changed, the bubble point of the fluid can be observed by means of representative electronic signals. These signals are then utilized in the preparation of bubble point pressure and fluid compressibility profile plots which can then be utilized for reservoir characterization.

The compressibility and viscosity of sample fluids are evaluated from PVT curves, and utilized in the calculation of fluid flow parameters in the reservoir.

The major features of PVT services are (1) to identify the type of fluid present in the formation prior to collection of samples, (2) to accomplish determination of down-hole bubble point pressure for optimum sampling conditions, (3) provide bubble point pressure and fluid compressibility data to enable the preparation of bubble point pressure and fluid compressibility profile plots for use in reservoir characterization, (4) to achieve over-pressure of the formation fluid sample to prevent phase separation on cooling and thereby provide for determination of fluid properties of the formation fluid for pressure transient analysis, and (5) to acquire downhole PVT data to check the validity of samples at the surface, either on location or at reservoir fluid laboratories.

The apparatus of the present invention performs pressure-volume-temperature (PVT) measurement down-hole with a sampling probe of the wireline formation tester seated against the formation of interest. One of its purposes is to determine the bubble point of formation fluid/gas samples collected from the formation. Another of its purposes is conducting bubble point pressure and fluid compressibility analysis at formation depth and conditions for use in the preparation of bubble point pressure and fluid compressibility profile plots for the purpose of reservoir characterization. Before or after a sufficient amount of formation fluid is purged from the formation into either a tank or to the borehole, the instrument performs a measurement of pressure, temperature and volume of a finite sample of the formation fluid. This feature can be accomplished by the use of a pump-through feature accomplished by a draw-down system having pump-through capability. This can also be done with a separate piston which does not pump through. The basic element of the draw-down system of the instrument is a bi-directional piston pump composed of a double-acting piston and valves to control positive displacement pumping, including the direction and volume of pumping. At least one of the cylinders of the piston pump is provided with a shutoff valve for fluid entrapment and is designated as a test chamber for conducting downhole bubble point and fluid compressibility analysis at formation depth for use in reservoir characterization. Precision temperature and pressure sensors are associated with the test chamber and a precision linear potentiometer is associated with the pump piston for detection of volumetric changes of the test chamber and the connate fluid entrapped therein during testing. The sensors and potentiometer provide electronic signal output which is utilized in bubble point pressure and compressibility profile plots which are interpreted for reservoir characterization. Hydraulic pressure provided by an on-board hydraulic pump is used to provide the power for piston movement of the pump. Solenoid valves, pilot valves, and/or check valves are used to control the piston pump action and direction and to control fluid entrapment for bubble point pressure and fluid compressibility analysis.

The primary pump element is a double-acting, bi- directional, positive displacement pump incorporating a reciprocating piston which provides pumping action in both stroke directions. This differs from existing draw-down piston pump designs, where the draw-down piston only provides pumping action in one direction. This capability allows for much more rapid pumping action when compared with the conventional one- directional pumping action. Conventional draw-down units provide pumping action in one piston movement direction, and a no-action return for the other piston direction.

The pump unit can be set to pump from bottom to top, or from top to bottom. This pumping direction is accomplished in situ by controllably positioning a four-way valve. This valve is controlled by an on-board computer which is contained in the downhole instrument.

The apparatus of the present invention achieves a controlled rate draw-down. The pump displacement rate can be controlled, thus allowing a controlled rate for pressure drop, total volume, or volume/second. This control allows improved test data by adapting the test to the formation characteristics.

The apparatus of this invention is also capable of pumping fluid from the formation of interest to the borehole. This may be beneficial in removing all filtrate, i.e., mud-cake from the formation before sampling or taking other data such as PVT. Resistivity and/or capacitance can also be measured while pumping. The pump can be set to control the fluid withdrawal rate of the draw-down module. The apparatus is also capable of achieving pumping in a direction opposite to the normal direction, i.e., from top to bottom rather than from bottom to top.

Piston displacement can be acceptably measured by a variety of means that are available within the state of the art. For example, piston displacement with a position sensor displacement can be detected by measuring piston movement by means of a variable resister or an inductive coil by the time required for an acoustic pulse to echo from one face of the pump piston or by the phase shift of a light beam when reflected from one face of the pump piston. Additionally, the volumetric displacement of the piston pump can be calibrated in the down- hole environment according to the mechanical limits for movement of the pump piston in either direction. By precisely measuring piston displacement, full control of the pump can be achieved. The reverse pumping capability of the pump system allows an unlimited volume of fluid to be pumped out of the sampling probe to clean any debris such as fine sand, rocks, flitrate, etc. that may exist on the sampling probe. The reversible pump direction also allows fluid to be injected from the tool or borehole into the formation. One example may be to inject completion fluid stored in a tank, or, fluid retrieved from the wellbore, or fluid previously pumped from the formation, into the formation. After injection of the completion fluid, additional draw-downs and/or sampling may take place to determine the effect of the completion fluid on the formation of interest.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 2 is a sectional view of a portion of the downhole multi-testing tool of FIG. 1, illustrating the bi-directional piston draw-down assembly thereof in position within the pump compartment of the instrument body.

FIG. 3 is a sectional view of the bi-directional piston pump mechanism of FIG. 2.

DETAILED DESCRIPTION OF PREFERRED EMBODIMENT

Figure 1:
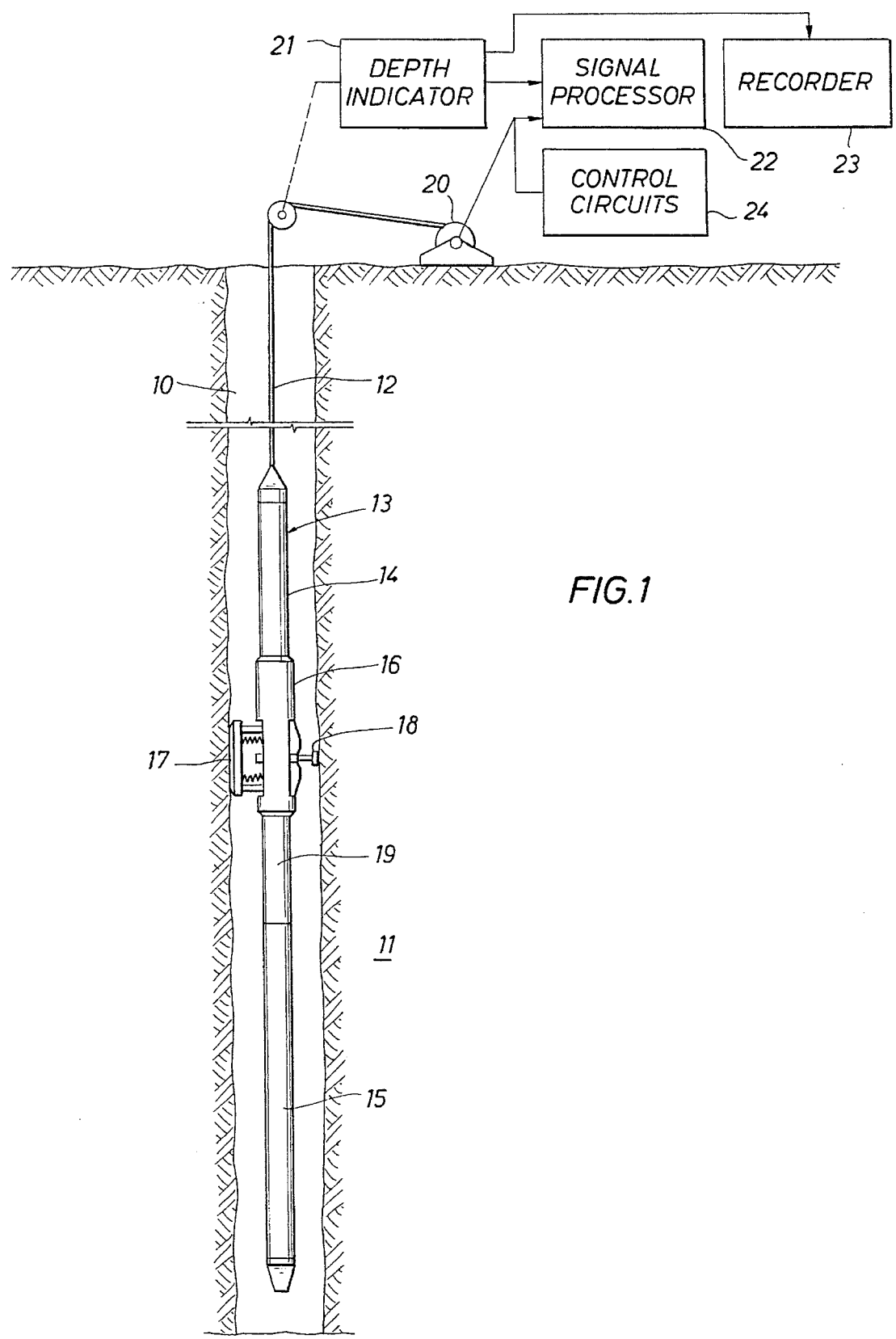
FIG. 1 is a pictorial view, partly in cross-section, of a formation test instrument constructed in accordance with the present invention and disposed in a borehole in sampling position with respect to a formation of interest and further showing a surface processing and control system therefor by way of block diagram schematics.

Referring now to the drawings in more detail, particularly to FIG. 1, there is illustrated schematically a section of a borehole 10 penetrating a portion of the earth formations 11, shown in vertical section. Disposed within the borehole 10 by means of a cable or wireline 12 is a sampling and measuring instrument 13. The sampling and measuring instrument is comprised of a hydraulic power system 14, a fluid sample storage section 15 and a sampling mechanism section 16. Sampling mechanism section 16 includes selectively extensible borehole wall engaging pad member 17, a selectively extensible fluid admitting sampling probe member 18 and bi-directional pumping member 19. The pumping member 19 could also be located above the sampling probe member 18 if desired. The sampling probe will include one or more packers, as shown schematically at 25 in FIG. 7, for engaging the well bore and isolating the fluid inlet passage thereof from the wellbore pressure which is typically significantly higher than formation pressure. Any other suitable packer systems may be employed for isolating the sampling probe from wellbore pressure to thus ensure that formation pressure or a pressure varying only slightly therefrom is introduced through the sampling probe to the various fluid circuits of the multitester tool.

In operation, sampling and measuring instrument 13 is positioned within borehole 10 by winding or unwinding cable 12 from hoist 20, around which cable 12 is spooled. Depth information from depth indicator 21 is coupled to signal processor 22 and recorder 23 when instrument 13 is disposed adjacent to an earth formation of interest. Electrical control signals from control circuits 24 are transmitted through electrical conductors contained within cable 12 to instrument 13.

Figure 7:
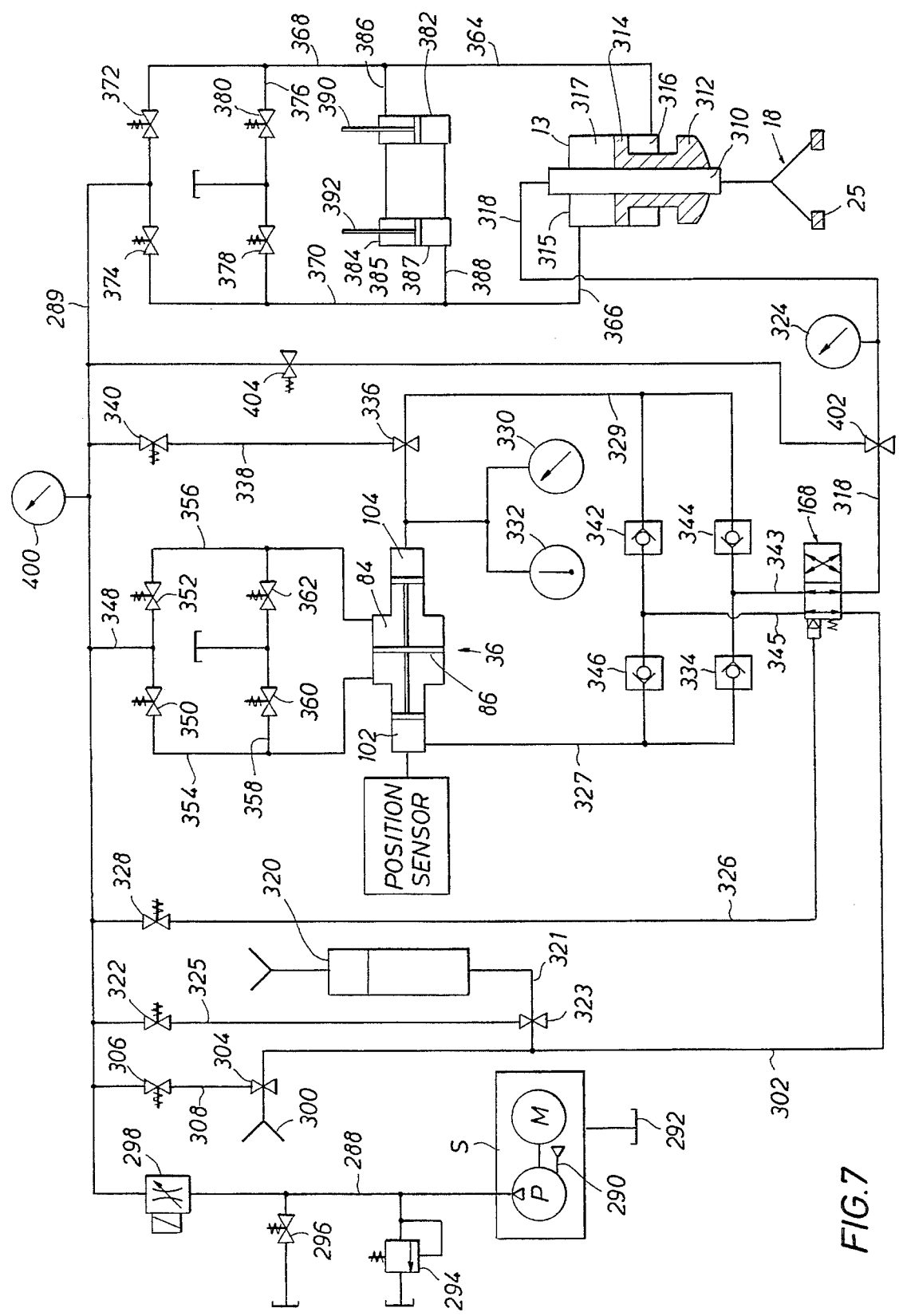
FIG. 7 is a hydraulic schematic illustration of fluid circuitry for operation and control of the double-acting, bi- directional formation draw-down and pump through system of this invention.

These electrical control signals activate an operational hydraulic pump within the hydraulic power system 14 shown schematically in FIG. 7, which provides hydraulic power for instrument operation and which provides hydraulic power causing the well engaging pad member 17 and the fluid admitting member 18 to move laterally from instrument 13 into engagement with the earth formation 11 and the bi-directional pumping member 19. Fluid admitting member or sampling probe 18 can then be moved into wellbore pressure isolated fluid communication with the earth formation 11. After such probe/formation communication has been established electrical control signals from control circuits 24 will selectively activate solenoid valves within instrument 13 for the taking of a sample of any producible connate fluids contained in the earth formation of intent.

Referring now to the partial sectional view of FIG. 2, there is illustrated a double ended, bi-directional pumping section of the sampling instrument, shown generally at 30 which will typically comprise a pumping member 19 of the multi-tester instrument. The pumping section 30 incorporates a double-acting bi-directional fluid control system having the capability of injecting a fluid medium, such as completion fluid for example, into a formation of interest and for withdrawing connate fluid from the formation. This feature permits downhole testing of the effect of a selected completion fluid on the formation intended to be completed for production. This apparatus is also capable of pumping injection fluid either from the wellbore or from a reservoir contained within the instrument and injecting the fluid into the formation. Additionally, the double-acting, bi-directional fluid control system has the capability of withdrawing connate fluid from the formation of interest and selectively discharging the fluid into the wellbore, such as for purging the system of debris such as fine sand, rocks, filtrate, and other foreign matter or selectively conducting the recovered connate fluid through the sampling system of the instrument. The bi-directional fluid control system is also constructed to define a test system for conducting bubble point pressure and fluid compressibility testing at formation depth. These and other features of the invention will become evident as the preferred embodiment of this invention is described in detail hereinbelow.

The pumping section 30 defines an elongate body structure 32 which is intended for use alone or in mechanically coupled relation with other sampling instrument components. This structure would contain appropriate cavities and passageways to accomplish the pumping circuitry illustrated in FIGS. 5, 6 and 7.

As shown in FIG. 2 the body structure 32 defines a pump cavity 34 within which is located a bi-directional piston pump shown generally at 36 and being shown in greater detail in FIG. 3. The piston pump 36 incorporates an elongate pump body 38 having upper and lower end connection members 40 and 42 which are sealed to the terminal body sections by annular seals 41 and 43. The end connection members are restrained against displacement from their sealed assembly with the terminal body sections by the body structure 32 or by other suitable means and are coupled by tubular projections 44 and 46 thereof which are received in sealed relation with body receptacles of the body structure 32. The pump 36 is also retained within the cavity or compartment 34 by means of retainer clamps 48 and 50 which are received about reduced diameter portions 52 and 54 of the pump body 38 and are secured to the body structure 32. The retainer clamps each function as connecting rings and serve to retain quick disconnect couplings 56 and 58 in sealed assembly with the body 32 and the pump body 38 so as to establish fluid communication between pump body operating fluid ports 60 and 62 and fluid passages 59 and 61 of the body 32 which are shown in FIG. 2. The intermediate portion of the pump body 56 is also retained in secured assembly with the body structure 32 by means of a retainer screw or bolt 64 which extends through a bolt opening in the body structure 32 and is threadedly received by the pump body 38.

The pump body 38 incorporates an intermediate body section 66 as best seen in FIG. 3 having internally threaded extremities 68 and 70, respectively to which are threadedly connected terminal body sections 72 and 74. The terminal body sections are sealed with respect to the intermediate body section 66 by means of annular seals 76 and 78, respectively.

The intermediate body section 66 and the terminal body section 74 cooperatively form an elongate internal pump chamber 80 having a cylindrical pumping chamber surface 82 forming a piston pumping chamber. A piston 86 partitions the pumping chamber 80 into variable volume pumping chambers 83 and 84 on respective sides of the piston. The piston is sealed with respect to the cylindrical pumping chamber surface 82 by means of an annular piston seal 88 and is reciprocated within the pumping chamber by hydraulic fluid selectively injected through pump chamber ports 60 and 62 into respective pumping chambers 83 or 84. From opposite sides of the piston 86 extend piston stems 90 and 92, each supporting respective high pressure seal assemblies 94 and 96 having sealing engagement with respective internal cylindrical surfaces 98 and 100 which respectively define pumping chambers 102 and 104. These pumping chambers are in communication respectively with tubular connector elements in tubular projections 46 and 106 which function to provide sealed fluid interchange between the respective pumping chambers of the piston pump and formation fluid flow passages which are defined by the instrument body structure 32. One of the pumping chambers may be designated as a valve controlled test chamber, as illustrated in greater detail in FIG. 11, for entrapping a known volume of connate fluid and conducting bubble point pressure and compressibility testing of the fluid so that the test results may be employed in bubble point pressure and compressibility profile plots for reservoir characterization. Tubular connector element 106 is sealed with respect to the pump body and the instrument body by means of annular seals. Thus, as hydraulic fluid functions to impart reciprocation to the piston 86 and its piston stems 90 and 92, the piston stems accomplish suction and pumping of formation fluid depending upon the direction of piston movement. As one pumping piston is moving in its power stroke for forcible ejection of formation fluid from its pumping chamber, the opposite piston will be moving in its suction stroke, drawing formation fluid into its pumping chamber for subsequent pumping displacement.

Terminal housing section 72 defines an internal position sensor chamber 110 which is sealed with respect to the pumping chamber 102 by means of a partition seal assembly 112. A position indicator stem 114 projects from the end portion of piston stem 90 and extends in sealed relation through the partition seal assembly 112 and into an internal receptacle defined within a position sensing potentiometer or other suitable piston position sensor 116. The output signals of the precision potentiometer are effectively used to determine known test chamber volume and volumetric change for the purpose of bubble point pressure and fluid compressibility testing. Electronic signals representing the position of the position indicator stem 114 within the potentiometer 116 are transmitted via electrical conductors 118 which extend through the tubular connector projection 44 to appropriate electrical circuitry within the instrument body 32. Thus, as the piston 86 is reciprocated within its chamber 84 this piston movement is sensed and transmitted electronically where it may be utilized for pumping control for pump calibration and for precision volumetric measurement, such as for determination of known volume and volumetric change of the test chamber.

The piston pumping capability achieved by the piston stems or plungers 90 and 92 is relatively small but this piston pumping activity may be achieved at significantly high pressure, i.e., in the order of 20,000 psi by controlling the relative pressure responsive dimensions of the piston 86 and the pump cylinder surfaces 98 and 100. In the event lower pressure, higher volume pumping is considered appropriate, a double-acting pump mechanism may be provided having larger diameter pump bores and piston plungers as compared with that shown in FIG. 3. In fact, since the double-acting, bi-directional piston pump 36 is preferably releasably secured within its cavity or receptacle, changing the pumping capacity of the modular bi-directional pumping section 30 may be simply achieved even under field conditions. After the protective cover 120 has been removed, the piston pump 36 will be exposed and may be simply and quickly removed through the use of readily available tools and replaced with a pump of different pumping capacity. Thus, if a different capacity pump is desired, or if the piston pump is in need of repair or replacement for any reason, this can be simply and efficiently accomplished even under field conditions in only a few minutes time, through the use of ordinarily available tools. This feature also permits a downhole multitester instrument without bubble point pressure testing capability to be readily converted, simply by changing out the bi-directional pump mechanism. Sealed fluid interconnection between the piston pump 36 and respective fluid passages of the body structure 32 may be of the plug-in type so as to simplify the installation and removal procedure for the pump. Each of the end fittings or connections members 40 and 42 are provided with connection projections of the plug-in type such as shown at 44 and 46 which are each provided with annular sealing elements for establishing seals within respective bores of the pump body. Likewise, the intermediate section of the piston pump is provided with a tubular connection element 106 having annular seals in seal grooves thereof for establishment of sealed interconnection with both the intermediate body section of the pump and the body structure 32.

Figure 4B:
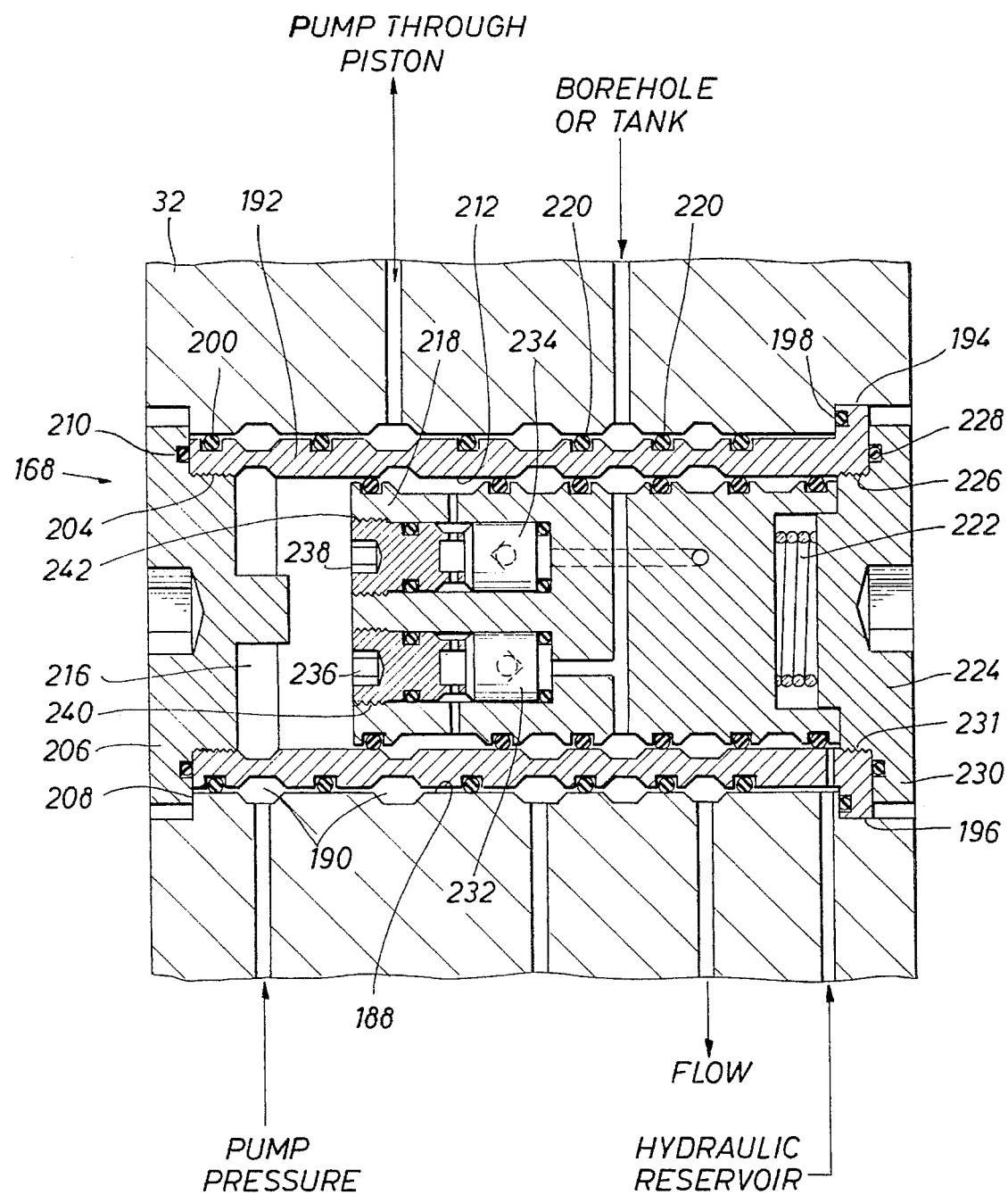
FIG. 4B is a sectional view of the pilot operated four- way formation fluid check valve assembly of FIG. 4A, with the valve mechanism being shown in the pilot operated position thereof.
Figure 4A:
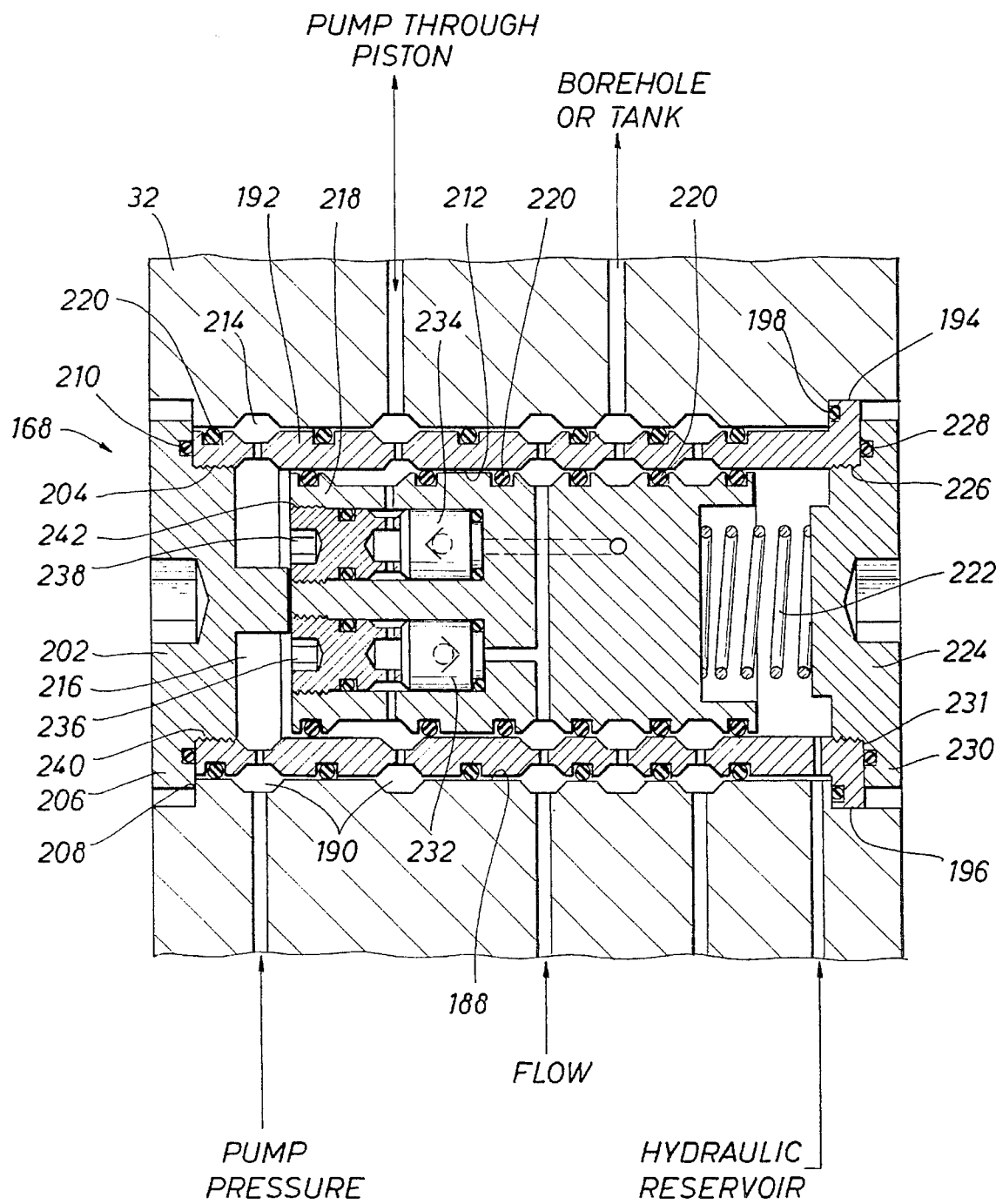
FIG. 4A is a sectional view of a pilot operated four- way formation fluid check valve assembly for selecting and reversing the pumping direction of the bi-directional piston pump mechanism of FIG. 3 and being shown in the normal position thereof.
Figure 5:
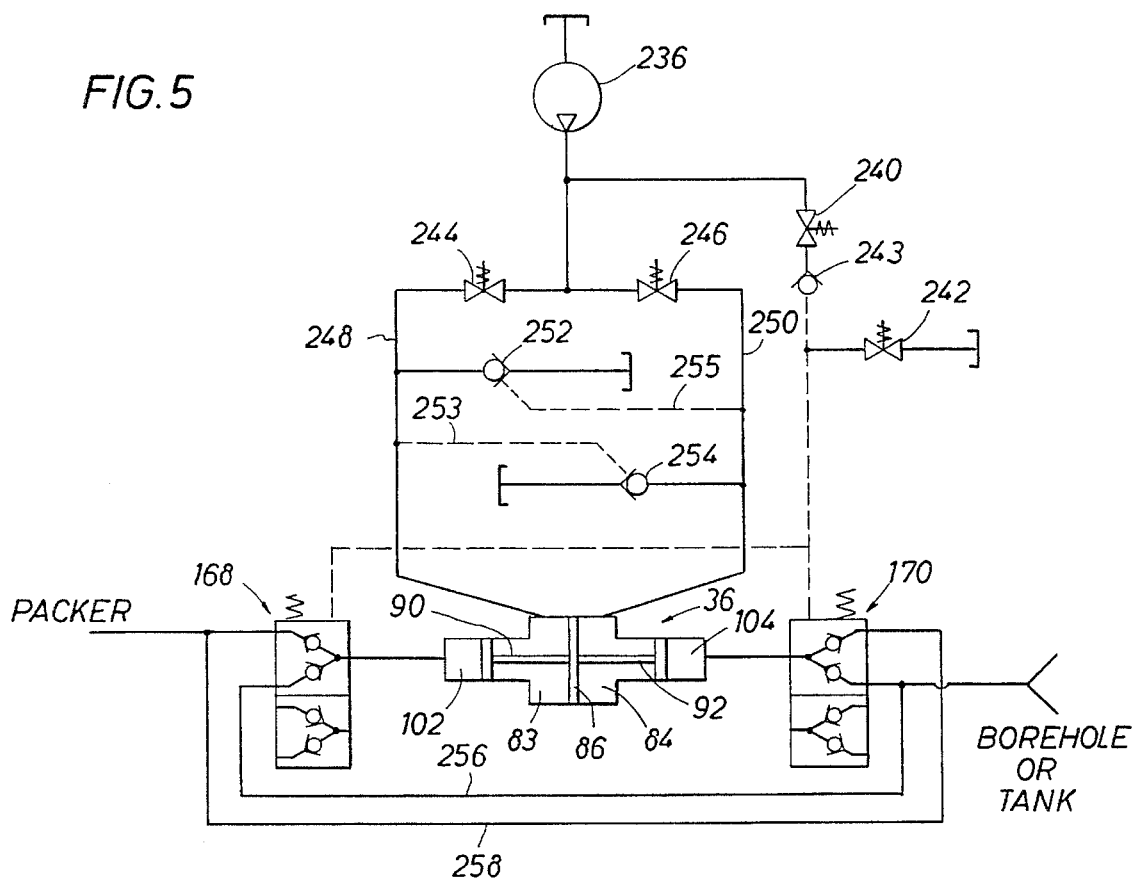
FIG. 5 is a hydraulic schematic illustration of the bi-directional piston pump mechanism of FIG. 3 together with hydraulic control circuitry for changing the direction of pump- through while the sampling instrument is located downhole.
Figure 6:
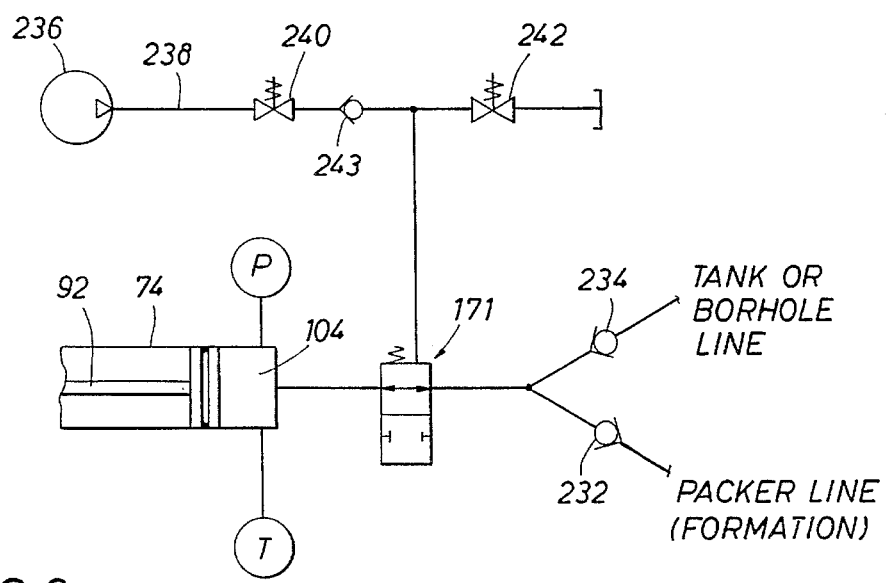
FIG. 6 is a partial hydraulic schematic illustration representing the addition of a pilot operated valve for confining a sample for PVT testing and illustrating solenoid control valving for positioning this valve.

In order to enable reversal of the pumping direction of the bi-directional piston pump 36 a pair of pilot operated control valve assemblies 168 and 170 are provided which are illustrated schematically in FIG. 5 and shown in the sectional view of FIGS. 4A and 4B. These control valves are generally referred to herein as "dirty fluid check valves" since they are employed to control the directional pumping of formation sample fluid and injection fluid through the various fluid passages of the instrument. Although these control/check valves 232 and 234 are of somewhat differing construction, they are mounted in a valve spool 218 which is shifted hydraulically under selective control from the surface such as by control circuits 24 or are shifted between operating positions under programmed control by control circuitry which is either located within the surface based circuits or within the instrument itself. From a standpoint of basic construction, the dirty fluid check valve mount assembly is generally in the form shown and described in connection with FIGS. 4A and 4B. The dirty fluid check valve shown generally at 168 and 170 in FIG. 5 is a hydraulically operated four-way check valve which has the function of changing the pump-through direction of the sampling instrument. A two way normally open hydraulically operated valve 170 shown in FIG. 6 is used to enable in situ PVT testing by the instrument.

With reference now to FIG. 4A, a representative example of the dirty fluid valve 168 is illustrated, this being a pilot operated four-way valve. The body structure 32 defines a plurality of fluid flow passages which are labeled as indicated, which passages are disposed in communication with a transverse valve bore 188. At the juncture of the respective passages with the valve bore, the valve bore is enlarged to define annular fluid conducting grooves such as shown at 190. A valve seat sleeve 192 is positioned within the bore 188 and defines a shoulder flange 194 which is seated against a circular internal stop flange 196 defined by an enlargement at one end of the bore 188. The valve sleeve is sealed with respect to the body structure by means of an annular sealing element 198 which engages the stop flange 196. At its opposite end the valve sleeve 192 is sealed with respect to the body structure 32 by means of an annular sealing element 200 which is seated against a portion of the cylindrical internal sealing surface defined by the valve bore 188. A valve retainer cover 202 is provided with an externally threaded section 204 which is received by an internally threaded internal portion of the valve sleeve 192 and defines an annular retainer flange 206 which engages an internal annular shoulder 208 to lock the valve sleeve in sealed, static position within the valve bore 188. The valve cover is sealed with respect to the valve sleeve 192 by means of a circular sealing element 210 which establishes sealing engagement with one end wall of the valve sleeve. The valve sleeve is of tubular configuration and defines an internal, cylindrical segmented sealing surface 212 which is interrupted by a plurality of internal fluid transfer grooves 214 and which establishes an internal valve chamber 216 within which is positioned a generally cylindrical valve spool element 218. The valve spool has sealed relation with respect to the internal cylindrical sealing surface segments 212 by means of a plurality of circular sealing elements 220.

The valve spool element 218 of FIGS. 4A and 4B, is shown to be urged in one direction by means of a compression spring 222 having one end thereof in force transmitting engagement with the valve spool element 218 and with the opposite end thereof in restrained engagement with a closure and retainer element 224 which establishes threaded connection with the valve sleeve at 226. An annular sealing element 228, carried by a circular seal groove in a radial sealing flange portion 230 of the retainer and closure element 224, establishes sealing engagement with an annular planar end surface 231 of the valve sleeve. It should be born in mind that the valve spool may be springless so that it does not receive a mechanically induced urging force. In the alternative, a similar valve may be provided having a valve spool that is hydraulically energized for movement in either direction and which is releasably retained at each of its positions by means of retainer detents. In the form of the invention shown in FIG. 4A, the valve spool element 218 is shown to define internal check valve chambers within which are shown a pair of check valve elements 232 and 234 by way of schematic illustration. The check valve elements 232 and 234 are retained within the valve spool by means of a pair of check valve retainers 236 and 238 which are threadedly received by outer, internally threaded portions 240 and 242 of the check valve receptacles. The check valve retainers 236 and 238 are sealed with respect to the valve spool element 218 by means of external annular sealing elements provided in seal grooves thereof.

As further shown in FIG. 4A, the valve spool element 218 is shown in the position for achieving flow from the packer to the borehole or to a sampling tank or vessel disposed internally of the instrument. As the piston pump mechanism is operated, therefore, movement of the bi-directional piston in one direction achieves suction induced flow of production fluid from the packer, tank or other source into the pump chamber. Since the packer is usually sealably disposed against a formation, this fluid is usually flitrate or formation fluid. If the packer is not seated, wellbore fluid would be pumped. By placing a cup shaped elastomeric seal around the tool between the packer and the wellbore exhaust port, drilling mud could be pumped by the bi- directional piston pump to urge the tool up-hole or down-hole. This bi-directional pump is the first practical means to develop sufficient pressure (100 psi approximates tool weight in 6¾ hole) to lift or otherwise shift a tool that has become differentially stuck. The output of the piston pump could also go to a pair of inflatable packers prior to being used to pump fluid into or from the "packed off zone". Adding large volume tanks could provide a small scale drill stem test. U.S. Pat. No. 4,535,843 broadly describes the pumping of fluid but does not practically address how to construct or control such a pump. When the direction of the piston is reversed, this recovered formation fluid is then pumped either to the wellbore such as for flushing away fine sand, rocks, mudcake or other debris that is present at the juncture of the sampling probe with the borehole wall at formation level. After all of the debris has been flushed into the wellbore, pumped flow is altered to permit pumping of formation fluid from the sampling probe into one or more sampling vessels for on-board storage, for subsequent downhole disposal or for ultimate transfer to the surface for laboratory testing.

The valving apparatus also has the capability of achieving pumping of liquid constituents, such as completion fluid, oil-water mixtures, either from a fluid reservoir in the instrument, or drilling mud from the borehole directly into the formation. This feature effectively enables the formation to be tested with a completion fluid so that the effect of the completion fluid may be determined prior to actual completion of the well or relative permeability to known viscosity fluid determined. Reversal of the direction of fluid pumping is achieved by applying hydraulic pressure from an operating pressure source located in the instrument to the pump pressure inlet passage shown at the upper left hand portion of FIG. 4B. Pressurized hydraulic fluid thus forces the valve spool element 218 downwardly, compressing the spring 222. Fluid present within the valve chamber 216 below the valve sleeve will be conducted through the valve sleeve to the hydraulic reservoir passage located at the lower left hand portion of FIG. 4B for return to the sump of the hydraulic fluid pump. In the position shown in FIG. 4A, operation of the bi-directional piston pump mechanism will induce fluid flow through the packer/sample passages of the valve mechanism and through the check valve 232 as the pump piston moves in one direction. As the direction of the pump piston is reversed, flow then is achieved through the opposite check valve 234, thereby forcing the collected formation sample through the borehole or tank passage shown at the lower right hand portion of FIG. 4 A. In the valve position shown in FIG. 4B the pumped fluid will flow through the borehole/tank passages of the valve mechanism and through the check valves 232 and 234 to the packer/sample passages of the instrument body as shown at the lower left hand portion of FIG. 4B. Flow of the collected formation sample to the borehole or sample tank is controlled by appropriate electronically selected, electrically or hydraulically energized valving.

Referring now to FIG. 6, there is shown a simplified schematic illustration of a portion of the downhole instrument to perform pressure-volume-temperature (PVT) measurement downhole with the wireline formation tester while seated against the formation. In cases where differential sticking is a problem, the sample could be taken into a tank after which the tool can be closed and moved slowly up or down the borehole while PVT analysis is conducted on the fluid in the sampling tank. One of its purposes is to determine the bubble point pressure and fluid compressibility of fluid/gas samples collected from the formation of interest so that the formation or formations may be characterized through use of this information. Before or after a sufficient amount of formation fluid is purged from the formation into either a tank or to the borehole, the multitester instrument can be controlled to perform a measurement of pressure, temperature and volume of a finite sample of formation fluid. This is accomplished by the use of the double-acting, bi-directional pump mechanism which includes a pump-through capability. The simplified schematic illustration of FIG. 6 discloses a hydraulic operating pressure supply pump 236 which discharges pressurized hydraulic fluid through a pilot pressure supply conduit 238 under the control of a pair of solenoid valves 240 and 242 and a check valve 243. These normally closed solenoid valves are selectively operated to direct the flow of hydraulic fluid from the hydraulic pump 236 to a normally open, two-way dirty fluid valve, shown generally at 171. A portion of the bi-directional pump mechanism of FIG. 3 is illustrated, showing one of the pistons stems 92 being reciprocable within the piston chamber 104. Pressure and temperature sensors "P" and "T" are in communication with the piston chamber 104 to thereby permit in situ inspection of the pressure and temperature of the formation fluid which is present within the piston chamber. Since the dirty fluid valve 171 is a normally open, two-way valve, in its open position as shown in FIG. 6, the pumped fluid from the piston chamber 104 is delivered through the valve assembly 170 to the check valves 232 and 234. When the piston stem 92 shown in FIG. 6 is moving to the left, it develops suction in the pumping chamber 104 which acts through the normally open valve 171, thereby inducing flow of formation fluid through the sampling probe and packer line from the formation of interest and across the check valve 232. When the piston stem 92 of the bi-directional pump mechanism is moving in the opposite direction, its discharge flow is achieved through the dirty fluid valve 171 and through the check valve 234 to the tank or borehole line. The flow of fluid to the sample collection tank or to the borehole is selected by using a solenoid control valve to shift a two-way dirty fluid valve that is located in a different section of the instrument.

As shown in the simple schematic illustration of FIG. 5, the bi-directional piston pump mechanism is illustrated generally at 36 with its pumping chambers 102 and 104 coupled in fluid communication with the dirty fluid check valve assemblies shown generally at 168 and 170. The bi-directional piston pump mechanism is capable of pumping from either of its pumping chambers 102 and 104 to the packer line or to the borehole- storage tank line, depending upon the position of the dirty fluid check valve mount assembly, as controlled by the positions of the respective solenoid valves 240 and 242 of the pilot pressure supply line 238. For reciprocating operation of the bi-directional piston pump mechanism, directional control valves 244 and 246 are selectively opened by an electrical control circuit, thereby directing pump pressure selectively to the pump pressure supply lines 248 and 250. Check valves 252 and 254 are provided in return line circuits to conduct hydraulic fluid from the respective variable volume pumping chambers 83 and 84 to the hydraulic storage reservoir of the hydraulic supply pump 236 and are selectively propped open by pressure via broken pilot pressure lines 253 and 255. A pair of directional flow lines 256 and 258 are coupled respectively to the packer line and to the borehole or supply tank line and function to direct pumped formation fluid or completion fluid from the respective pumping chambers 102 and 104 in a direction selected by the position of the dirty fluid check valve mount assemblies 168 and 170. By simply reversing the direction of pumping, the bi-directional, double-ended pump 36 has the capability of pumping fluid either into the formation or from the formation and pumping collected formation fluid either into a sample collection vessel or into the wellbore. These features provide significant advantage from the standpoint of downhole testing flexibility.

An alternative method for reversing flow is illustrated in FIG. 7. In this case a four-way valve switches inlet/outlet lines to rigidly mounted dirty fluid check valves. The hydraulic circuitry of the wireline downhole testing instrument is illustrated schematically in FIG. 7 and shows a hydraulic fluid supply line 288 being the discharge line of a hydraulic fluid pump "P" which is driven by an electric motor "M". The electric motor is powered and controlled through appropriate electrical circuitry from the surface based equipment shown in FIG. 1. The pump "P" derives its source of hydraulic fluid from a sump "S" via a suction line 290. The pump and motor are preferably contained within the hydraulic fluid reservoir which is the sump for the purpose of cooling, but such is not intended to limit the scope of this invention. The symbol "292" where it occurs in the hydraulic circuitry, represents the return of hydraulic fluid to the sump "S".

Pressure within the supply line 288 is limited by a pressure relief valve 294 which relieves excessive pressure to the sump. Pressure in the hydraulic supply line 288 is selectively vented to the sump upon operation of a normally closed solenoid valve 296. The line pressure of supply line 288 is selected for desired pressure level for operation of the various hydraulic fluid circuits of the downhole sampling instrument by means of an electrically operated variable flow resistor 298.

For PVT testing of the formation of interest it is appropriate to establish communication of the sampling probe or admitting member 18 with the subsurface formation of interest which is traversed by the wellbore. Symbol "300" is representative of the wellbore at formation level. Admission of fluid to and from the wellbore is accomplished by means of a sampling circuit 302 having a pilot operated isolation valve 304 to which hydraulic pressure is supplied via a solenoid valve 306 in branch hydraulic fluid supply line 308.

The fluid admitting member shown generally at 18 includes a movable sampling probe 310 which is movable laterally from the instrument 13 in conjunction with a hydraulically energized probe actuating piston 312 having its piston portion 314 received within a hydraulic cylinder 315 that is provided within the instrument body and partitioning the cylinder into hydraulic chambers 316 and 317. The sampling probe 310 is hydraulically energized independently of the piston 312. A sample line 318 in communication with the fluid passage of the sampling probe 310 is coupled with a pilot operated four-way dirty fluid check valve assembly 168. This valve, when positioned as shown in FIG. 7, establishes connection of line 318 with suction, discharge lines 327 and 329 via check valves 334 and 344 depending upon the direction of movement of the pump piston 86. The sampling circuit 302 is connected to the suction discharge lines of the pump 36 via line 345 and check valves 342 and 346 through the dirty fluid check valve assembly discussed hereinbelow and is also coupled with at least one sample collection tank 320 under the control of a pilot operated valve 322 and an isolation valve 323. The pressure within the sample line 318 is detected by a pressure sensor 324 which may be an absolute pressure gauge as schematically illustrated or which may take any other suitable form.

It is desirable that the downhole testing and sample collection instrument have the capability of varying the pressure of the formation fluid from actual formation pressure level for the purpose of conducting certain downhole, in situ testing, such as bubble point pressure and fluid compressibility testing, and also for the purpose of conducting certain laboratory testing of the formation fluid collected within the sample collection tank 320. For example, by withdrawing fluid from a formation at a pressure above the bubble point pressure fluid samples which have not undergone phase separation can be recovered and delivered to a laboratory for testing by sufficiently elevating the pressure of the formation fluid above its bubble point pressure to allow cooling to surface temperature without dropping the pressure in the tank below the bubble point pressure. It is desirable, therefore, that the instrument have the capability of elevating the pressure of the collected formation fluid to a differential pressure range of about 20,000 psi for this particular purpose. To accomplish pressure variation of the formation fluid sample, also referred to herein as "dirty fluid", the pilot operated four-way valve shown generally at 168 is coupled in selected, pilot controlled communication with the sample lines 302 and 318. This valve receives its pilot pressure energization from the supply line 289 via pilot pressure supply line 326 under the control of a solenoid valve 328.

The double-acting, bi-directional piston pump mechanism illustrated generally at 36 and described above in connection with FIG. 3 is connected with its respective pump chambers 102–104 in connection with suction discharge lines 327 and 329 respectively. The pumping pressure of the pump mechanism is sensed by an absolute pressure gauge 324. For PVT analyses the pressure and temperature of the formation fluid is sensed by a pressure gauge 330 and a temperature sensor 332.

With the dirty fluid check valve 168 at its normally open position as shown in FIG. 7, the suction stroke of pumping chamber 102 will induce the flow of formation fluid through the sampling probe 310, sample line 318, valve 168, line 343, check valve 334 and flow line 327 to the pumping chamber 102. At the same time the double-acting piston pump 36 discharges formation fluid from the pumping chamber 104 and through the flow line 329 when the pilot operated normally closed control valve 336 is open by pressure supplied through conduit 338 upon opening of the normally closed solenoid valve 340. The formation fluid, thus pressurized by the piston pumping system, flows through check valve 342 and connector line 345 to the sample line 302. With the pilot operated valve 323 open by energization of the normally closed solenoid valve 322 via pressure supply line 325, the pressurized formation fluid is caused to enter the sample tank 320 via sample tank line 321. When the direction of the piston pump 36 is reversed, pumping chamber 104 becomes the suction chamber and pumping chamber 102 becomes the pressure chamber. In this case, the flow of formation fluid from the sample line 318 occurs through the valve 168 and check valve 344 and through line 329 and open valve 336 into the chamber 104. At the same time, the piston of the piston pump 36 develops pressure in pumping chamber 102 thereby discharging pressurized formation fluid through line 327 and check valve 346 to the dirty fluid check valve 168 through line 345. This pressurized formation fluid is conducted to the sample tank 320 under circumstances when the pilot operated valve 323 is open by introduction of pilot pressure through line 325 when solenoid valve 322 is energized to its open position. At this time pilot operated valve 304 will be closed, thus isolating the pressurized formation fluid from the formation. For discharge of the fluid being pumped through sample line 302 into the wellbore valve 304 will be opened by pilot pressure supplied through open solenoid valve 306 while tank supply solenoid valve 323 will be closed.

As the piston pump 36 is operated, the position of its piston 86 is precisely detected at all times by the position sensor shown schematically in FIG. 7 and shown at 114–116 in FIG. 3. This feature permits precision measuring of piston displacement versus time of displacement and also permits precision measuring of finite test chamber volume and volumetric change for the purpose of determining bubble point pressure and fluid compressibility of the connate fluid. The precision pressure and temperature gauges 330 and 332 also provide precise pressure and temperature data to provide the instrument with precision volumetric measurement of fluid being extracted from the formation. Additionally, the double-acting, bi-directional piston pump may be effectively calibrated in the downhole environment to achieve pumping at a rate that is determined by formation production capability. To accomplish this feature, the actuating fluid system of the piston pump 36 receives hydraulic pumping pressure via branch supply line 348 upon selective controlled opening and closing of the pump actuating solenoid valves 350 and 352 thus selectively pressurizing pump operating pressure supply lines 354 and 356. Obviously when one supply line 354 or 356 is pressurized to thus pressurize one of the variable volume pumping chambers 83 or 84, the opposite piston pumping chamber must be vented to permit fluid displacement. This feature is accomplished through the provision of a vent line 358 which is coupled to the sump and which is controlled by selectively opened solenoid valves 360 and 362. Thus, the solenoid valves 350, 352, 360 and 362 are cycled electronically so as to achieve selective operation of the piston pump 36. Further, these valves are selectively controllable electronically so as to achieve precision piston reciprocation to thereby achieve precision volumetric fluid measurement capability. Since the precise position of the piston 86 is known at all times, data reflecting the rate of piston movement is also indicative of the rate of fluid pumping into the formation or the rate of fluid recovery from the formation. Precision piston detection also permits downhole calibration of the pump to be accomplished by electronically adjusting cycling of controls and/or adjusting the pressure of the hydraulic fluid supply, such as by varying the pressure control of the electronically controlled fluid flow resistor 298.

Upon selective opening of the solenoid valve 328 for pressurization of the pilot pressure supply line 326 the four-way dirty fluid check valve 168 will be shifted to its reverse flow position so that pumped fluid under pressure from either of the pumping chambers 102 or 104 will be delivered through check valves 342 and 346 respectively to the connector line 345 where it is conducted through the shifted dirty fluid check valve 168 and caused to flow through sample line 318 to the sampling probe 310 and thence into the formation. The fluid being injected into the formation may be recovered from the sample tank 320 via open valve 323 and sample line 302, thus precluding any necessity to retrieve the sampling instrument for the purpose of sample collection disposal. Further, with the valve 168 in its normal position as shown in FIG. 7, and with the valve 323 closed and valve 304 open, samples of formation fluid being pumped may be delivered into the wellbore to thus provide a virtually unlimited flushing capacity to remove filtrate from formation. By reversing the dirty fluid check valve 168 and with valve 304 open, collected formation fluid, perhaps including certain testing fluids such as completion fluid, may be recovered from the wellbore and reinjected by the bi-directional piston pumping mechanism through the sampling probe 310 into the formation. For this reason, disposal of formation fluid or sampling fluid or a combination of the two, i.e., flitrate, may be disposed of by pumping it into the formation for dispersal into the fluid medium contained within the formation. Further, the instrument is capable of pumping virtually unlimited quantities of testing fluid, such as completion fluid from the wellbore into the formation or pumping testing, fluid from on-board storage tanks into the formation and then recovering treated formation fluid for in situ testing and/or for laboratory testing.

For operation of the sampling probe, the energized probe actuations piston 312 is operated by injection of pressurized fluid into respective piston chambers 316 or 317 via supply conduits 364 and 366 respectively. For this purpose, hydraulic pressure is supplied via supply line 289 which contains pressure regulated hydraulic oil. Flow resistor 298 regulates the pressure in supply line 289 from surface setting via control circuit 24 and electronic feedback control to control the pressure detected by supply line pressure gauge 400 to branch supply lines 368 and 370 via solenoid energized control valves 372 and 374. Obviously, when one of the piston chambers is being supplied with pressurized hydraulic fluid, the opposite piston chamber must be vented. For this purpose, a hydraulic vent circuit 376 is coupled across conduits 368 and 370 and is vented to the hydraulic sump upon selective opening of solenoid valves 378 and 380. A pair of pad actuating cylinder 382 and 384 are provided, each having internal chambers that are coupled to supply lines 386 and 388 so as to simultaneously supply selected cylinder chambers 385 or 387 with hydraulic pressure. The piston stems 390 and 392 of the pad actuating cylinders simultaneously impart force to operating plungers for borehole wall engaging pad 17 of FIG. 1.

With valving set as in FIG. 4A, a small volume change (in the range of from 5 cc to 20 cc and preferably about 10 cc) can be made. This change would be called a "draw down" test. In this test, which is commonly run with conventional formation pressure testers, the pressure in the instrument as measured by gauge 324 shown at the bottom right hand portion of FIG. 7 first decreases below formation pressure and then increases or "builds up" to formation pressure as flow from the formation repressurizes volume of fluid between the formation and the piston chamber 104 or 102. The larger this volume, the longer is the time required for "build up" to formation pressure. It is desirable to reduce the total time required for pressure testing; therefore, the volume between the formation and the displacement needs to be as small as possible. Practical considerations for physical separation between the packer and the pump suggest that a valve is needed immediately after the pressure gauge 324 and the packer 25. Adding a piloted two-way normally open valve 402 and a solenoid control valve 404, it is possible to stop the draw down as soon as flow from the formation has begun and allow the pressure to recompress only the fluid between valve 402 and the formation. Pressure gauge 324 is in this line to accurately measure formation pressure. Since piston displacement is also measured in relation to time and can be correlated with pressure, all of the data necessary for a pressure transient analysis is available at the time valve 404 is closed.

Since the bi-directional piston pump can be used to repeat tests, one method would be to draw-down in several very small increments of volume, such as 1 cc, and closing valve 402 after each increment and observe whether or not the pressure increases. If not, the next increment would be made until build-up is observed. In each instance the volume to be repressurized is minimized so that repressurization time is minimized.

An alternative method of detecting that flow has begun is to monitor the pressure time response with gauge 324 until a plot of the derivative of the pressure versus time shows that spherical flow has begun (a negative half slope is observed). Valve 402 is then closed, the pump stopped, and pressure build-up is observed. This assures acquisition of valid data with minimum disturbance of the formation.

With the sampling probe 310 in fluid communicating engagement with the formation of interest, the bi-directional piston pump mechanism is operative and selectively controllable to extract formation fluid from the formation, to inject a fluid medium into the formation, to pump the formation fluid so recovered into a sampling tank or to pump the formation fluid into the wellbore. The reversible piston pump 36 is capable of recovering a fluid from onboard fluid storage or from the wellbore and injecting it into the formation. This feature is especially important from the standpoint of testing the formation for the effect of a testing fluid such as completion fluid. This invention effectively permits the pumping of fluids of differing viscosity for the purpose of evaluating the characteristics of a formation as determined by the relative viscosity of the formation fluid and the injected fluid. The relative viscosity of the fluids can be of considerable importance from the standpoint of formation productivity, including secondary recovery from the formation of interest. The bi-directional piston pump of this invention can also achieve pumping to and from the formation or the wellbore. Continuous pumping from the formation into the wellbore may occur for the purpose of clearing the formation interface of debris such as filter cake, fine sand, rocks, etc., thereby permitting the taking of a clean sample for purpose of downhole testing. All of these features can be accomplished without removal of the formation testing instrument from the wellbore. One of the more important features of this invention is the capability of investigating formation pressure, versus time and the capability of correlating it with volume versus time. This capability has not heretofore been available in downhole testing instruments.

Figure 8:
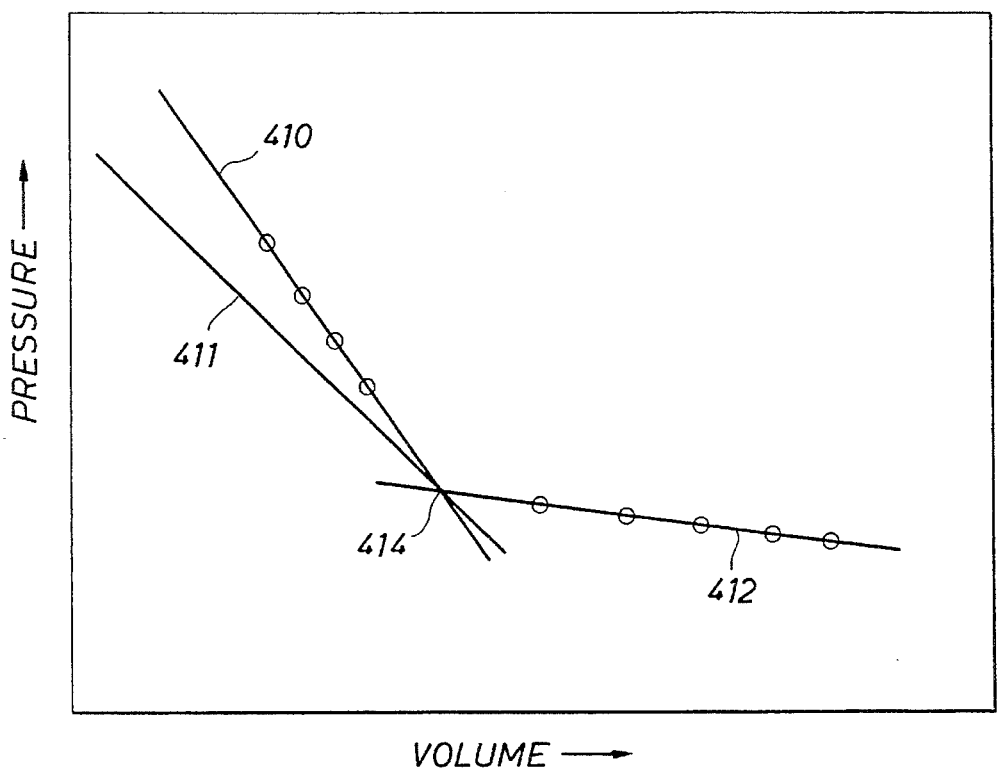
FIG. 8 is a graphical representation illustrating the use of a pressure vs volume plot to determine the bubble point and compressibility of a fluid.

With reference now to FIG. 8, bubble point pressure is determined by confining fluid in a known volume and by observing pressure changes as the volume of the fluid sample is changed. A plot of fluid volume against pressure will indicate fluid phase change from one phase (liquid), as shown by line 410, into two phases (liquid and gas), as shown by line 412. The intersection of two best fit lines, as shown at 414 indicates the bubble point pressure for the sample fluid. Line 411 is representative of variations in fluid compressibility.

Fluid compressibility is calculated as follows:

$$\text{Compressibility} = \frac{1}{V2} * \frac{(V2 - V1)}{(P1 - P2)}$$

where:
V1=Volume at higher pressure
V2=Volume at lower pressure
P1=Higher pressure
P2=Lower pressure A typical room temperature value for water is $3.3 \times 10^{-6}$ psi and for crude oil is $60 \times 10^{-6}$ psi, which illustrates that compressibility can also differentiate between oil and water.

Figure 9:
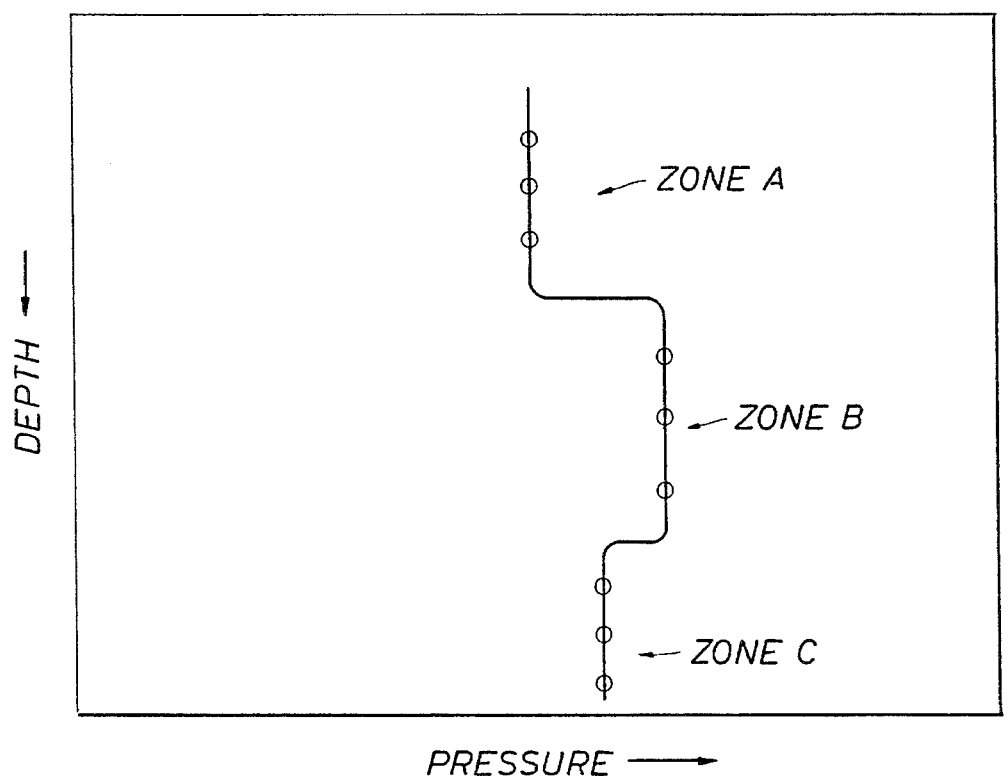
FIG. 9 is a graphical representation illustrating the use of bubble point pressure vs formation depth to identify different subsurface production zones.

Referring now to FIG. 9, when bubble point pressure is determined at several depths within a petroleum well, a plot of bubble point pressure against depth is expected to be constant. When this is true, it is likely that tests were conducted on the same fluid. However, if bubble point pressure is different, then different types of fluid were tested and therefore two or more different reservoirs exist. For example, as shown in FIG. 9, bubble point pressure tests identify fluid from three production zones A, B and C.

Figure 10:
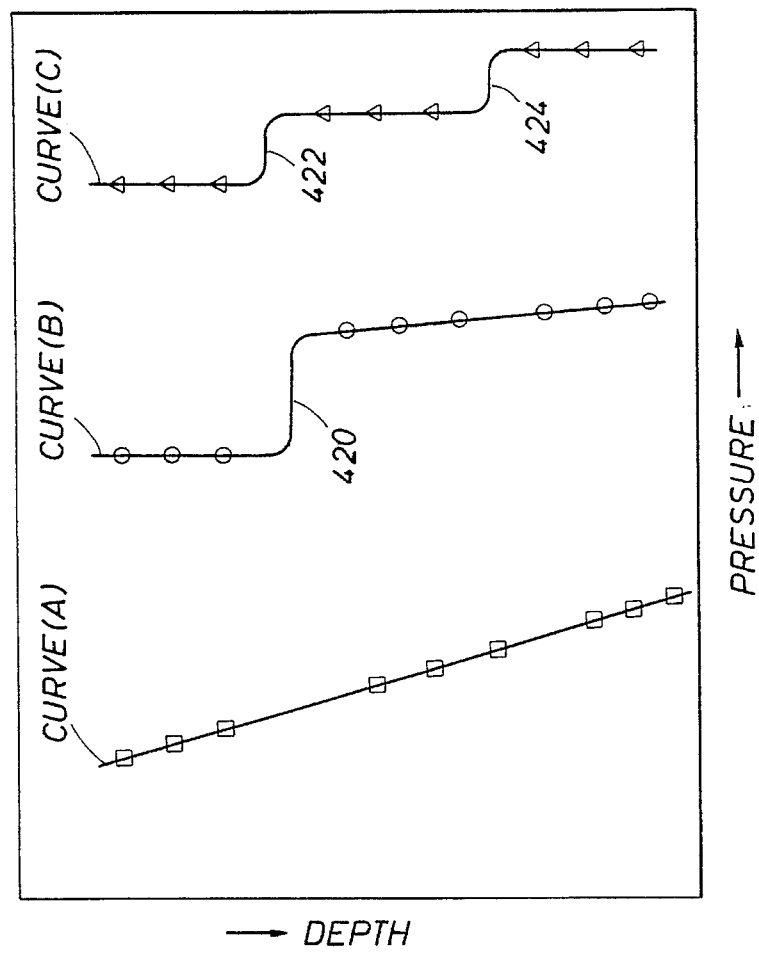
FIG. 10 is a graphical representation illustrating how adding compressibility plotted vs depth can identify different subsurface fluid production zones which have the same fluid pressure.

Referring now to FIG. 10, the graphical representation illustrates three different profile plots of the same subsurface formation in comparison and thus shows how reservoir characterization can be erroneous or incomplete depending on the profile plotting system that is employed. By comparing the curves of FIG. 10 a reservoir having plural zones is identified. The Fig. also indicates how adding fluid compressibility plotted vs formation depth can identify different subsurface production zones which have the same bubble point pressure. Curve "A" is representative of a conventional pressure gradient plot, which substantially defines a straight line, and thus establishes a pressure trend indicating the presence of a single production formation from which the sample fluid is emanating. It is readily seen that, by reliance on curve "A" alone, the actual character of the reservoir does not become recognized. Curve "B" is representative of a bubble point pressure profile which defines a sharply configured offset at 420, thus providing evidence of production fluid emanating from two disconnected subsurface formations. Curve "C" is representative of fluid compressibility (single phase) and indicates by sharply defined offsets at 422 and 424 that three different types of fluids are emanating from the formations defining this particular formation interval.

Figure 11:
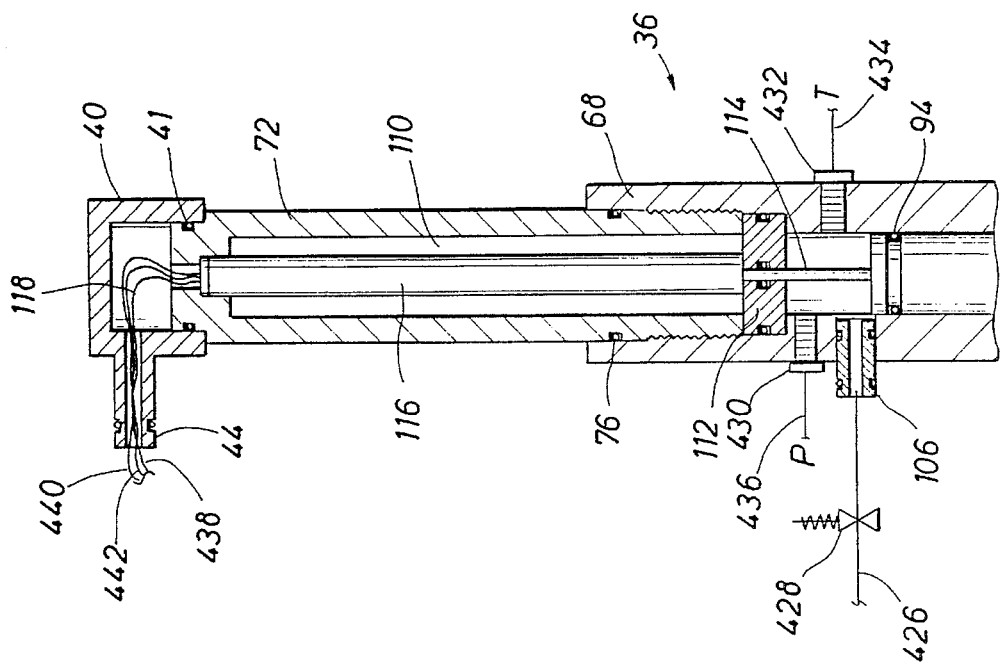
FIG. 11 is a mechanical and electrical schematic illustration of a portion of the bi-directional piston pump mechanism of the present invention which constitutes a test chamber and system for conducting bubble point pressure and fluid compressibility analysis at formation depth.

FIG. 11 is a partial sectional view of one of the cylinder and piston assemblies of the present invention representing a bubble point pressure and fluid compressibility test chamber and which also serves as a piston pumping chamber for the pump-through capability of the downhole PVT multitester instrument. FIG. 11 also provides illustration of hydraulic and electrical circuitry by way of schematics. The supply line or passage 426 for pump chamber 102 is provided with a solenoid operated shutoff valve 428 for entrapment of a finite volume of connate fluid within the pump chamber, thus defining the pump chamber as a test chamber for bubble point pressure and fluid compressibility testing. The test chamber is provided with precision pressure and temperature sensors 430 and 432 respectively, to which are coupled electronic signal conductors 434 and 436., respectively, that provide signal output "T" and "P" at the surface equipment representing the temperature and pressure of the fluid sample. The precision linear potentiometer 116 is provided with electrical power supply conductors 438 and 440 and includes a position signal output conductor 442 for delivery at the surface equipment of signals representing the position of the piston stem 90 and thus the volume at any point of time of the test chamber 102. For testing, the piston can be precisely located within its cylinder after having drawn in a finite volume of connate fluid as indicated by position signals of the potentiometer. The shutoff valve can then be closed to entrap the sample. After this has been done the pump mechanism may be hydraulically energized to change the volume of the test chamber and thus the volume of the entrapped finite volume of fluid. Observation of the pressure change of the fluid sample during the volume change thereof will be indicative of the bubble point pressure of the fluid. Although a linear type pump cylinder and piston arrangement for bubble point pressure testing has been described above, this invention is not intended to be limited thereby. The multitester instrument may be constructed to establish any suitable variable volume testing chamber the volume of which being sensed in any suitable fashion. Any suitable precision temperature and pressure sensors may be employed within the spirit and scope of this invention.

It has been discovered that bubble point pressure determination plots and bubble point pressure and compressibility profile plots are precise, comprehensive and are more reliable than the conventional pressure gradient plots from the standpoint of reservoir characterization. They have a number of significant advantages in comparison with pressure gradient plots. They are useful in the identification of vertical reservoir continuity in the same reservoir and in fact are more reliable than the conventional pressure gradient method for vertical reservoir continuity. With a pressure gradient profile curve, different types of fluid from different formations may follow the same pressure gradient trend, thereby providing an incorrect indication of a single formation. With the method of the present invention even though different fluids may follow the same pressure gradient trend and have the same bubble point pressure, fluid compressibility will indicate that different fluids are present.

The present method and apparatus may also be employed to identify the drive mechanism of the formation, such as depletion or gas cap drive, for example. If the formation pressure is higher than the bubble point pressure of its fluid, the drive mechanism constitutes a depletion drive of which dissolved gas separates from the fluid and creates the driving influence for flow of the formation fluid toward the well bore. In such case secondary recovery by pressure maintenance is needed to optimize production from this type of formation. If the formation pressure is lower than the bubble point pressure of the fluid being sampled, a gas cap exists, and the flow process driving the formation fluid toward the well bore is due to gas cap expansion. The system of the present invention can also be utilized for identification of low formation pressure, which provides indication that the formation is substantially depleted and thus cannot be effectively produced even under conditions of secondary recovery. The present invention also provides information to define optimum flowing pressure to control gas separation from the connate fluid, thereby enabling the producer to maximize recovery by effective control of production pressure.

In view of the foregoing, it is evident that the present invention is one well adapted to attain all of the objects and features hereinabove set forth, together with other objects and features which are inherent in the apparatus disclosed herein.

As will be readily apparent to those skilled in the art, the present invention may be produced in other specific forms without departing from its spirit or essential characteristics. The present embodiment, is therefore, to be considered as illustrative and not restrictive, the scope of the invention being indicated by the claims rather than the foregoing description, and all changes which come within the meaning and range of the equivalence of the claims are therefore intended to be embraced therein.

What is claimed:

1. A method for acquiring and testing the formation fluid of a subsurface earth formation having a wellbore defined therein and containing formation fluid, comprising:

(a) positioning within a wellbore a formation testing instrument having a sampling probe and having a bi-directional piston pump having opposed pumping chambers therein each being in valve controlled reversible pumping communication with said sampling probe for selective pumping of completion fluid into and from said subsurface earth formation and having pump pistons in said opposed pumping chambers being in fixed relation with one another and being simultaneously linearly movable and having at least one sample tank within said formation testing instrument, said bi-directional piston pump having an operating piston chamber having an operating piston therein being in fixed driving relation with said pump pistons;

(b) projecting said sampling probe from said formation testing instrument into sampling communication with said subsurface earth formation;

(c) controllably operating said bi-directional piston pump in one selected pumping direction for forcing a quantity of a selected completion fluid through said sampling probe and into said subsurface earth formation;

(d) controllably operating said bi-directional piston pump in the opposite pumping direction for pumping formation fluid from said subsurface formation through said formation testing instrument and into said wellbore to flush away any contaminants present in the surface of said wellbore at said sampling probe until uncontaminated formation fluid is present within said formation testing instrument;

(e) controllably operating said bi-directional piston pump in the opposite selected pumping direction for, pumping a quantity of said uncontaminated formation fluid from said subsurface earth formation through said sampling probe and into said formation testing instrument; and (f) conducting at least one test on said formation fluid within said formation testing instrument.

2. The method of claim 1 wherein said formation testing instrument having electronic test signal generating circuitry therein and signal processing circuitry being provided at a surface location for processing electronic fluid test signals, said conducting at least one test comprising:

(a) performing at least one formation fluid test on said formation fluid within said testing instrument and developing electronic signals representing the results of said formation fluid test; and (b) transmitting said electronic signals from said formation testing instrument to said signal processing circuitry.

3. The method of claim 1 wherein said formation testing instrument defines internal fluid circuits having valves for control thereof and having first and second valve settings, said method further comprising:

after said withdrawing step, selectively routing said formation fluid by first valve settings of said valves from said subsurface earth formation through said fluid circuits and into said sample tank and by second valve settings of said valves selectively routing said formation fluid from said subsurface earth formation through said fluid circuits of said formation testing instrument into said wellbore.

4. The method of claim 1, wherein said formation testing instrument defining an on-board completion fluid supply and including completion fluid circuitry therein having instrument valving for selectively connecting said bi-directional piston pump for pumping completion fluid from said on-board completion fluid supply or said wellbore and said forcing of said quantity of completion fluid through said sampling probe and into said subsurface earth formation comprises:

(a) with said bi-directional piston pump and said instrument valving of said completion fluid circuitry selectively establishing a predetermined pumping direction and pumping said quantity of completion fluid from said wellbore or said onboard completion fluid supply and into said subsurface earth formation by means of said bi-directional piston pump;

(b) reversing the pumping direction of said bi-directional piston pump from said predetermined pumping direction by selectively positioning of said instrument valving; and (c) accomplishing said control! ably operating said bi-directional piston pump for pumping said formation fluid from said subsurface earth formation into said testing instrument by means of said bi-directional piston pump in said reversed pumping direction thereof and selectively routing said formation fluid into said formation testing instrument for testing or through said formation testing instrument and into said wellbore for flushing contaminants from said subsurface earth formation.

5. The method of claim 1, wherein said formation testing instrument defines fluid formation circuits therein having instrument valving in said fluid circuits being selectively positioned for controlling the direction of formation fluid flow through said fluid circuits and wherein:

(a) said forcing of said quantity of a selected completion fluid comprises establishing pump directional control of said bi-directional piston pump by selective positioning of said instrument valving, and pumping said selected completion fluid from said formation testing instrument through said sampling probe and into said subsurface earth formation;

(b) reversing pump directional control of said bi-directional piston pump by selective positioning of said instrument valving; and (c) said withdrawing step comprising pumping formation fluid from said subsurface earth formation through said sampling probe and into said formation testing instrument by said bi-directional piston pump.

6. The method of claim 5, wherein contaminant material is present in said subsurface earth formation at said wellbore and wherein:

(a) after said withdrawing step, causing selective positioning of said instrument valving to communicate said fluid circuits of said formation testing instrument with said wellbore; and (b) pumping formation fluid from said formation through said formation testing instrument and into said wellbore for flushing of said contaminant material from said subsurface earth formation.

7. The method of claim 5, wherein said sample tank of said formation testing instrument having a completion fluid therein, said method including:

(a) after said withdrawing step, causing selective positioning of said instrument valving to communicate said sample tank with said sampling probe through said bi-directional piston pump; and (b) with said bi-directional piston pump, pumping said completion fluid from said sample tank through said sampling probe for flushing said contaminants from said subsurface earth formation at said wellbore.

8. The method of claim 1, wherein said subsurface earth formation has a formation pressure and said bi-directional piston pump of said formation testing instrument comprises a double-acting, bi-directional piston pump and wherein production fluid pressure, volume and temperature testing means is located within said formation testing instrument, said method comprising:

(a) after said withdrawing a quantity of said formation fluid from said subsurface earth formation through said sampling probe and into said formation testing instrument by controlled reciprocation of said bi-directional piston pump, changing said formation pressure of said sample of said formation fluid by controlled linear movement of said double-acting, bi-directional piston pump; and (b) selectively conducting production fluid pressure, volume and temperature tests on said pressure changed sample of said formation fluid.

9. The method of claim 8, wherein said production fluid pressure, volume and temperature measurement tests are influenced by contaminants, said method further comprising:

repeating said pressure, volume and temperature tests until a non-contaminated production fluid sample has been obtained from said subsurface earth formation as indicated by said pressure, volume and temperature testing means.

10. The method of claim 1, wherein said operating piston chamber being located intermediate said pumping chambers and having said pump pistons fixed to and extending from each side of said operating piston, said formation testing instrument further having electronic position indicator means for at least one of said operating piston and pump pistons and being adapted for generating electronic position signals, said method comprising:

(a) with said bi-directional piston pump set in a selected pumping direction, controllably reciprocating said operating piston for driving said pump pistons;

(b) detecting positions of at least one of said operating piston or said pump pistons within said bi-directional piston pump with said electronic position indicator means;

(c) generating electronic position signals with said electronic position indicator means being representative of said detected positions; and (d) correlating said electronic position signals with time of pump piston movement to identify the volume of formation fluid pumped by said bi-directional piston pump mechanism.

11. The method of claim 10, including:

electronically varying said volume of formation fluid pumped by said bi-directional piston pump.

12. A method for acquiring and testing the formation fluid of a subsurface earth formation having a wellbore defined therein and containing formation fluid:

(a) positioning within a wellbore a formation testing instrument having a sampling probe and having a bi-directional piston pump having opposed pumping chambers therein each being in valve controlled reversible pumping communication with said sampling probe for selective pumping of wellbore fluid into and from said subsurface earth formation and having pump pistons in said opposed pumping chambers being in fixed relation with one another and being simultaneously linearly movable and having at least one sample tank within said formation testing instrument, said bi-directional piston pump having an operating piston chamber having an operating piston therein being in fixed driving relation with said pump pistons;

(b) projecting said sampling probe from said formation testing instrument into sampling communication with said wellbore at said subsurface earth formation;

(c) controllably operating said bi-directional piston pump in one selected pumping direction for forcing a quantity of wellbore fluid through said sampling probe and into said subsurface earth formation to flush contaminants therefrom;

(d) controllably operating said bi-directional piston pump in the opposite selected pumping direction for withdrawing a quantity of said formation fluid from said subsurface earth formation through said sampling probe and into said formation testing, instrument:

(e) conducting at least One test on said formation fluid within said formation testing instrument;

(f) detecting the temperature of formation fluid being withdrawn from said subsurface earth formation;

(g) correlating said detected formation fluid temperature with a volume of formation fluid pumped to establish the temperature corrected precision quantity of formation fluid pumped by said bi-directional piston pump.

13. A method for acquiring and testing the formation fluid of a subsurface earth formation having a wellbore defined therein and containing formation fluid:

(a) positioning within a wellbore a formation testing instrument having a sampling probe and having a bi-directional piston pump having opposed pumping chambers therein each being in valve controlled reversible pumping communication with said sampling probe for selective pumping of wellbore fluid into and from said subsurface earth formation and having pump pistons in said opposed pumping chambers being in fixed relation with one another and being simultaneously linearly movable and having at least one sample tank within said formation testing instrument, said bi-directional piston pump having an operating piston chamber having an operating piston therein being in fixed driving relation with said pump pistons;

(b) projecting said sampling probe from said formation testing instrument into sampling communication with said subsurface earth formation;

(c) controllably operating said bi-directional piston pump in one selected pumping direction for forcing a quantity of wellbore fluid through said sampling probe and into said subsurface earth formation to flush contaminants therefrom;

(d) controllably operating said bi-directional piston pump in the opposite selected pumping direction for withdrawing a quantity of said formation fluid from said subsurface earth formation through said sampling probe and into said formation testing instrument:

(e) conducting at least one test on said formation fluid within said formation testing instrument (f) detecting the temperature of formation fluid being withdrawn from said subsurface earth formation;

(g) capturing a selected volume of said formation fluid within at least one of said pumping chambers of said formation testing instrument by precision linear positioning said pump pistons within at least one of said pumping chambers; and (h) correlating said selected volume of said formation fluid with said detected formation fluid temperature for precision determination of temperature corrected volume thereof.

14. A method of for acquiring and testing the formation fluid of a subsurface earth formation having a wellbore therein and containing a formation fluid, wherein said formation fluid has a bubble point pressure, comprising:

(a) positioning within a wellbore a formation testing instrument having a sampling probe and having a bi-directional piston pump having opposed pumping chambers therein each being in valve controlled reversible pumping communication with said sampling probe for selective pumping of wellbore fluid into and from said subsurface earth formation and having pump pistons in said opposed pumping chambers being in fixed relation with one another and being simultaneously linearly movable and having at least one sample tank within said formation testing instrument, said bi-directional piston pump having an operating piston chamber having an operating piston therein being in fixed driving relation with said pump pistons, at least one pumping chamber of said bi-directional piston pump receiving said formation fluid during linear pump piston movement in one direction and from which said formation fluid is expelled upon linear pump piston movement in the opposite direction during pumping activity, said at least one pumping chamber further being a bubble point pressure and fluid compressibility test chamber of said formation testing instrument, said formation testing instrument further having means for sensing the temperature of said formation fluid, the pressure of said formation fluid within said bubble point pressure and fluid compressibility test chamber and sensing the volume of said test chamber, said pump piston trapping said formation fluid within said bubble point pressure and fluid compressibility test chamber;

(b) projecting said sampling probe from said formation testing instrument into sampling communication with said subsurface earth formation:

(c) controllably operating said bi-directional piston pump in one selected pumping direction for forcing a quantity of wellbore fluid through said sampling probe and into said subsurface earth formation to flush contaminants therefrom:

(d) controllably operating said bi-directional piston pump in the opposite selected pumping direction for withdrawing a quantity of said formation fluid from said subsurface earth formation through said sampling probe and into said formation testing instrument;

(e) conducting at least one test on said formation fluid within said formation testing instrument:

(f) trapping a finite volume of said formation fluid within said bubble point pressure and fluid compressibility test chamber;

(g) measuring the pressure and volume of said trapped finite volume of formation fluid and providing electronic signals representative thereof;

(h) controllably changing the volume of said trapped finite volume of formation fluid;

(i) observing pressure changes of said trapped finite volume of trapped formation fluid during volume change thereof;

(j) determining the bubble point pressure of said formation fluid by comparison of said formation fluid pressure, volume, volume change and pressure change; and (k) utilizing said bubble point pressure of multiple formation fluid tests for reservoir characterization of said subsurface earth formation.

15. A method for flushing debris from a subsurface earth formation having a wellbore defined therein and for acquiring uncontaminated samples of formation fluid from said subsurface earth formation and for testing said formation fluid for bubble point pressure, said method comprising:

(a) positioning within a wellbore of a subsurface formation a formation testing instrument having a sampling probe for fluid communicating engagement with said subsurface earth formation and having an on-board sample tank and having a double acting bi-directional piston pump therein being in selective pumping communication with said sampling probe and with said on board sample tank, said double acting bi-directional piston pump having a pump body defining a pair of pumping chambers and having an operating chamber located between said pumping chambers and a pump drive member having pump pistons fixed thereto and located within said pumping chambers and an operating piston fixed to said pump drive member and being located within said operating chamber, a valve controlled hydraulic operating circuit being located within said formation testing instrument and inducing selective linear movement to said operating piston for linear pumping movement of said pump drive member and said pump pistons, said formation testing instrument further having means therein for conducting volume temperature and formation pressure tests on said formation fluid;

(b) projecting said sampling probe from said formation testing instrument into sampling communication with said subsurface earth formation;

(c) inducing selective reciprocating movement to said operating piston and said pump pistons by said hydraulic fluid operating circuit for pumping formation fluid from said subsurface earth formation through said formation testing instrument and into said wellbore for fluid flushing of contaminants from said subsurface earth formation at said wellbore until uncontaminated formation fluid is recovered from said subsurface earth formation;

(d) selectively reciprocating said pump pistons for pumping a quantity of said uncontaminated formation fluid from said subsurface earth formation and into said onboard fluid tank;

(e) conducting volume, temperature and formation pressure tests on said uncontaminated formation fluid within said formation testing instrument; and (f) pumping uncontaminated formation fluid into said sample tank for analysis following removal of said formation testing instrument from said wellbore.

16. The method of claim 15, wherein at least one of said pumping chambers of said formation testing instrument is adapted for conducting bubble point pressure tests therein, said method including:

(a) after said pumping step (c) of claim 15, compressing said formation fluid within said at least one pumping chamber to a pressure level exceeding bubble point pressure of said formation fluid; and (b) maintaining said pressure level of said formation fluid to prevent phase separation thereof; and (c) conducting bubble point analysis of said formation fluid within said at least one pumping chamber.

17. The method of claim 15, including:

(a) separating said sampling probe from said subsurface formation after said quantity of said uncontaminated formation fluid has been pumped into said sample tank; and (b) conducting tests of uncontaminated formation fluid with said formation testing instrument within said wellbore and separated from said subsurface earth formation.

18. The method of claim 17, including:

moving said formation testing instrument within said wellbore while conducting said formation fluid tests.

19. Apparatus for conducting pressure, volume and temperature tests of a connate fluid sample from a subsurface earth formation having a wellbore defined therein and for obtaining samples of connate fluid contained within said subsurface earth formation, comprising:

(a) an instrument body structure for positioning at a selected formation depth within a wellbore of a subsurface earth formation and having at least one connate fluid sample tank therein for selectively receiving connate fluid and for containing testing fluid, said instrument body structure further having means internally thereof for conducting volume, pressure and temperature tests on said connate fluid within said instrument body structure;

(b) a sample probe being laterally extensible from said instrument body structure for fluid sampling engagement with said subsurface earth formation, said sample probe defining a fluid sampling passage for admitting the connate fluid from said subsurface earth formation to said instrument body structure and for transferring the testing fluid from said sample tank of said instrument body structure to said subsurface earth formation;

(c) a double acting bi-directional piston pump having a pump body being located within said instrument body structure and having a pair of spaced and interconnected pump cylinders therein and pump pistons being linearly movable within said pump cylinders said double acting bi-directional piston pump further having an operating cylinder and having an operating piston being fixed to said pump pistons and being movable within said operating cylinder and having a hydraulic circuit for controlled reciprocation of said operating piston and pump pistons;

(d) a hydraulic fluid pumping circuit having check valves permitting unidirectional flow of fluid to and from said pumping chambers and being located within said instrument body structure for selectively controlling pumping direction of said double acting bi-directional piston pump for selective pumping of said testing fluid from said fluid tank through said sampling probe into said subsurface earth formation and pumping of the connate fluid from said subsurface earth formation through said sampling probe and into said instrument body structure; and (e) a hydraulic fluid reversing valve being located in said hydraulic fluid pumping circuit for selecting the direction of hydraulic fluid flow to and from said check valves.

20. The apparatus of claim 19, wherein said conducting means comprises:

(a) position sensing means being located within said instrument body structure for sensing position of said piston of said bi-directional piston pump and generating electronic piston position signals; and (b) means located at the surface receiving and processing said electronic piston position signals for identification of the volume of connate fluid pumped by said bi-directional piston pump.

21. The apparatus of claim 20, wherein said conducting means comprises:

(a) means within said instrument body structure for detecting pressure and temperature of connate fluid entering said formation testing instrument from said subsurface earth formation and generating electronic pressure and temperature signals relating thereto; and (b) means located at the surface for processing said electronic pressure and temperature signals in correlation with said electronic piston position signals for derivation of pressure and temperature corrected volumetric displacement of said connate fluid by said piston pump.

22. The apparatus of claim 20, wherein said position sensing means comprises:

(a) a position indicator rod extending from one of said pump pistons of said double acting bi-directional piston pump; and (b) a linear movement potentiometer receiving said position indicator rod therein and generating said electronic piston position signals reflecting the position of said position indicator rod relative to said linear movement potentiometer and thus reflecting the position of said pump piston within said pumping cylinder.

23. The apparatus of claim 19, wherein:

(a) said operating piston chamber being located intermediate said pumping chambers, and said pump body further having;

a connate fluid circuit being located within said instrument body structure and being in communication with said pumping chambers of said bi-directional piston pump and receiving connate fluid from said pumping chambers upon reciprocation of said pumping pistons;

connate fluid flow reversing means being located within said connate fluid circuit and for selectively directing the flow of connate fluid within said connate fluid circuit to said subsurface earth formation or from said subsurface earth formation and having a first flow controlling position directing connate fluid flow from said subsurface earth formation to said pumping chambers and from said pumping chambers to said connate fluid sample tank, said flow reversing means having a second flow controlling position directing connate fluid flow from said pumping chambers to said subsurface earth formation; and means within said connate fluid circuit for controllably positioning said connate fluid reversing means at said first or second flow controlling positions.

24. The apparatus of claim 23, wherein said connate fluid circuit includes a completion fluid source within said instrument body structure and said connate fluid reversing means comprises:

(a) a flow reversing valve within said connate fluid circuit having a first flow controlling position directing connate fluid flow from said subsurface earth formation to said pumping chambers and from said pumping chambers to said sample tank, said flow reversing valve having a second flow controlling position directing completion fluid from said completion fluid source to said pumping chambers and from said pumping chambers to said subsurface earth formation; and (b) means for controllably positioning said flow reversing valve at said first or second flow controlling positions.

25. The apparatus of claim 24, wherein said means for controllably positioning said flow reversing valve comprises:

(a) a pilot pressure supply being operatively coupled to said flow reversing valve; and (b) a control valve selectively controlling application of pilot pressure from said pilot pressure supply to said reversing valve for selected operating thereof to said first and second flow controlling positions.

26. The apparatus of claim 24, wherein said flow reversing valve comprises:

(a) a valve seat sleeve being retained in sealed relation within said instrument body structure and forming a plurality of internal sealing surface segments, said valve seat sleeve having spaced annular external fluid conducting grooves disposed in communication with respective hydraulic pump operation circuit and connate fluid circuit of said instrument body structure, said valve seat sleeve further having a plurality of internal annular fluid conducting grooves separating said internal sealing surface segments;

(b) a valve spool being movably positioned in sealed relation within said valve seat sleeve and defining spaced external annular fluid conducting grooves in selective communication with said annular internal fluid conducting grooves of said valve seat sleeve and having internal fluid conducting passages; and (c) means selectively hydraulically shifting said valve spool from said first flow controlling position to said second flow controlling position.

27. The apparatus of claim 26, wherein said valve spool includes:

first and second check valve controlled passages being defined within said valve spool and each permitting unidirectional flow of connate fluid and being selectively operable depending upon the position of said valve spool to permit selective pumped flow of connate fluid to said bi-directional piston pump from said subsurface earth formation for flushing of contaminants from said subsurface earth formation and from said subsurface earth formation to said wellbore during flushing of contaminants from said subsurface earth formation and being positionable to direct pumped flow of connate fluid from said subsurface earth formation to said sample tank.

28. The apparatus of claim 26, including:

selecting means within said instrument body structure for directing the pumped flow of connate fluid through said flow reversing valve to said wellbore or to said sample tank and to direct completion fluid from said completion fluid source to said subsurface earth formation.

29. The apparatus of claim 28, wherein said selecting means comprises:

(a) a flow passage being located within said instrument body structure and connecting said passages of said flow reversing valve with said wellbore and said sample tank; and (b) at least one control valve in said flow passage for selectively controlling the flow of connate fluid from said flow reversing valve to said wellbore or to said sample tank.

* * * * *